US012760276B2

(12) United States Patent
Itescu et al.

(10) Patent No.: US 12,760,276 B2
(45) Date of Patent: Oct. 13, 2026

(54) EXPANSION OF HEMATOPOIETIC STEM CELLS

(71) Applicant: Mesoblast International Sarl, Meyrin (CH)

(72) Inventors: Silviu Itescu, Melbourne (AU); Paul Simmons, Melbourne (AU)

(73) Assignee: MESOBLAST INTERNATIONAL SARL, Meyrin (CH)

( * ) Notice: Subject to any disclaimer, the term of this patent is extended or adjusted under 35 U.S.C. 154(b) by 1368 days.

(21) Appl. No.: 17/286,972

(22) PCT Filed: Oct. 31, 2019

(86) PCT No.: PCT/EP2019/079865
§ 371 (c)(1),
(2) Date: Apr. 20, 2021

(87) PCT Pub. No.: WO2020/089411
PCT Pub. Date: May 7, 2020

(65) Prior Publication Data

US 2021/0388319 A1 Dec. 16, 2021

(30) Foreign Application Priority Data

Oct. 31, 2018 (AU) ................................ 2018904125

(51) Int. Cl.
*C12N 5/0789* (2010.01)
*A61K 35/28* (2015.01)

(52) U.S. Cl.
CPC ............ *C12N 5/0647* (2013.01); *A61K 35/28* (2013.01); *C12N 2501/065* (2013.01); *C12N 2501/125* (2013.01); *C12N 2501/145* (2013.01); *C12N 2501/2303* (2013.01); *C12N 2501/2306* (2013.01); *C12N 2501/26* (2013.01); *C12N 2502/1358* (2013.01); *C12N 2510/00* (2013.01)

(58) Field of Classification Search
CPC . C12N 5/0647; C12N 2501/065; A61K 35/28
See application file for complete search history.

(56) References Cited

U.S. PATENT DOCUMENTS

| | | | | |
|---|---|---|---|---|
| 9,301,978 | B2 * | 4/2016 | Itescu | A61P 37/02 |
| 11,261,429 | B2 * | 3/2022 | Chaurasia | A61P 35/02 |
| 2018/0187156 | A1 * | 7/2018 | Rossi | A61P 1/04 |
| 2019/0085291 | A1 * | 3/2019 | Sauvageau | A61K 35/28 |

OTHER PUBLICATIONS

Koh et al. (Biochem Biophys Res Commun. Apr. 16, 2005;329(3):1039-45. doi: 10.1016/j.bbrc.2005.02.077., referenced in IDS submitted Apr. 5, 2024, (Year: 2005).*

Koh et al. (Biochem Biophys Res Commun. Apr. 15, 2005;329(3):1039-45. doi: 10.1016/j.bbrc.2005.02.077., referenced in IDS submitted Apr. 5, 2024, (Year: 2005).*

Goncalves et al. (Exp Hematol. Oct. 2006;34(10):1353-9. doi: 10.1016/j.exphem.2006.05.024, referenced in IDS submitted Apr. 5, 2024, (Year: 2006).*

Lima et al. (N Engl J Med. Dec. 13, 2012;367(24):2305-15. doi: 10.1056/NEJMoa1207285., referenced in IDS submitted Apr. 20, 2021, (Year: 2012).*

Koh, Sang Hyeok, et al. "Co-culture of human CD34+ cells with mesenchymal stem cells increases the survival of CD34+ cells against the 5-aza-deoxycytidine-or trichostatin A-induced cell death." Biochemical and Biophysical Research Communications 329.3 (2005): 1039-1045.

Murphy, Matthew B., Kathryn Moncivais, and Arnold I. Caplan. "Mesenchymal stem cells: environmentally responsive therapeutics for regenerative medicine." Experimental & molecular medicine 45.11 (2013): e54-e54.

Williams, Emma L., Kate White, and Richard OC Oreffo. "Isolation and enrichment of Stro-1 immunoselected mesenchymal stem cells from adult human bone marrow." Stem Cell Niche: Methods and Protocols (2013): 67-73.

Arulmozhivarman, Guruchandar, et al. "Zebrafish in-vivo screening for compounds amplifying hematopoietic stem and progenitor cells:—preclinical validation in human CD34+ stem and progenitor cells." Scientific reports 7.1 (2017): 12084.

Burba, Ilaria, et al. "Histone deacetylase inhibition enhances self renewal and cardioprotection by human cord blood-derived CD34+ cells." PLoS One 6.7 (2011): e22158.

Lau, Show Xuan, et al. "Human mesenchymal stem cells promote CD34+ hematopoietic stem cell proliferation with preserved red blood cell differentiation capacity." Cell biology international 41.6 (2017): 697-704.

Lo Iacono, Melania, et al. "Wharton's jelly mesenchymal stromal cells as a feeder layer for the ex vivo expansion of hematopoietic stem and progenitor cells: a review." Stem Cell Reviews and Reports 13.1 (2017): 35-49.

Gonçalves, Raquel, et al. "A Stro-1+ human universal stromal feeder layer to expand/maintain human bone marrow hematopoietic stem/progenitor cells in a serum-free culture system." Experimental hematology 34.10 (2006): 1353-1359.

Gronthos, Stan, et al. "A novel monoclonal antibody (STRO-3) identifies an isoform of tissue nonspecific alkaline phosphatase expressed by multipotent bone marrow stromal stem cells." Stem cells and development 16.6 (2007): 953-964.

An Aug. 12, 2022 Written Opinion issued by the Intellectual Property Office of Singapore in connection with the counterpart Singapore Application No. 11202103901Y, filed Oct. 31, 2019.

Kumar S. & Geiger H., HSC Niche Biology and HSC Expansion Ex Vivo. trends Mol Med, Aug. 8, 2017, vol. 23, No. 9 (Exhibit 2).

Chaurasia, P. et al. "Epigenetic reprogramming induces the expansion of cord blood stem cells." Journal of Clinical Investigation, B M J Group, vol. 124, No. 6, Jun. 2, 2014, pp. 2378-2395.

(Continued)

*Primary Examiner* — Fereydoun G Sajjadi
*Assistant Examiner* — Joel D Levin
(74) *Attorney, Agent, or Firm* — John P. White

(57) ABSTRACT

The present disclosure relates to methods and compositions for expansion of human hematopoietic stem cells. The present disclosure also relates to methods of treatment involving the use of the expanded HSCs.

20 Claims, 14 Drawing Sheets

(56) References Cited

OTHER PUBLICATIONS

De Lima, M. et al. "Cord-Blood Engraftment with Ex Vivo Mesenchymal-Cell Coculture. " The New England Journal of Medicine, vol. 367, No. 24, Dec. 13, 2012, pp. 2305-2315.
International Search Report issued Jan. 24, 2020 in connection with PCT International Application No. PCT/EP2019/079865.
Written Opinion (form PCT/ISA/237) issued Jan. 24, 2020 in connection with PCT International Application No. PCT/EP2019/079865.

* cited by examiner

**Culture *without* MPC**

Culture *without* MPC

SFT + VPA

Culture + MPC

Culture + MPC

EXPANSION OF HEMATOPOIETIC STEM CELLS

CROSS-REFERENCE TO RELATED APPLICATIONS

This application is a § 371 national stage of PCT International Application No. PCT/EP2019/079865, filed Oct. 31, 2019, claiming priority of Australian Patent Application No. 2018904125, filed Oct. 31, 2018, the contents of each of which are hereby incorporated by reference herein.

TECHNICAL FIELD

The present disclosure relates to methods and compositions for expansion of human hematopoietic stem cells (HSCs). The present disclosure also relates to methods of treatment involving the use of the expanded HSCs.

BACKGROUND

Hematopoietic stem cells (HSCs) possess the unique capacity to self-renew and give rise to all types of mature cells within the blood and immune systems. These features have provided widespread clinical utility of HSC transplantation, although major sources of HSCs (human bone marrow, mobilized peripheral blood, and umbilical cord blood) remain limited as a donor supply. These problems are compounded by the need to seek out well-matched donors to recipients, thereby adding heightened complexity in ensuring a suitable and reliable supply of donor material. Further, patients suffering from disease resulting from a genetic mutation would benefit greatly from gene therapy techniques, wherein autologous material is manipulated ex vivo, and returned following correction of the corrected genetic defects. In various types of transplant categories, developing effective techniques for ex vivo expansion and genetic manipulation of HSCs could provide a ready, renewable resource outside of the existing donor infrastructure and establish new gene therapy techniques to treatment of diseases caused by genetic mutation.

Unlike in the case of embryonic stem cells (ESCs), expansion of HSCs in culture in general is at the expense of loss of primitive phenotype or "sternness". It is unclear whether extrinsic factors can be applied to enhance expansion of HSC populations without loss of "sternness". Thus, there remains a need for methods for generating and expanding large numbers of human HSCs to increase the availability of cells for transplantation as a renewable therapeutic resource.

SUMMARY OF THE DISCLOSURE

The Applicant has developed methods for expanding HSCs from a starting population of hematopoietic cells derived from any source including adult, umbilical cord blood, iPS cells, fetal or embryonic sources. In one embodiment the method preferentially expands the primitive HSCs within a starting population of hematopioetic cells. The primitive HSCs have the phenotype CD34+, CD45RA−, CD90+, CD49f+.

The ability to expand HSCs in this manner is advantageous for transplantation and other therapies for hematology and oncology diseases and disorders. As described in the methods herein, HSC numbers can be significantly increased ex vivo. A method of increasing stem cell numbers is useful for autologous donor transplants which often lack sufficient stem cells. A method to increase stem cell numbers also enables umbilical cord blood to be useful for adult patients, thereby expanding the use of allogeneic transplantation.

Accordingly, the present disclosure provides a method of expanding hematopoietic stem cells, comprising culturing a population of hematopoietic cells in the presence of mesenchymal lineage precursor or stem cells (MLPSCs) and at least one histone deacetylase inhibitor (HDACi) such that hematopoietic stem cells having the phenotype CD34+ are expanded.

In one example, hematopoietic stem cells having the phenotype CD34+, CD90+ are expanded. In another embodiment hematopoietic stem cells having the phenotype CD34+, CD90+, $CD45RA^{-}$ are expanded In another embodiment hematopoietic stem cells having the phenotype CD34+, CD45RA−, CD90+, CD49f+ are expanded In another embodiment hematopoietic stem cells that are CD34+, CD45RA−, CD90+, CD49f+ are preferentially expanded compared to hematopoietic stem cells that are CD34+, CD49f−.

In one embodiment an increase of the number of CD34+ cells of at least 20-fold, or at least 30-fold, or at least 40-fold, or at least 5-fold, or at least 60-fold, or at least 70-fold or at least 80-fold or at least 90-fold or at least 100-fold is indicative of HSC expansion.

In one embodiment, the starting cell population is cultured for a time sufficient to reach an absolute number of CD34+ cells of at least $10^5$, $10^6$, $10^7$, $10^8$ or $10^9$ cells.

In one embodiment, the total number of CD34+, CD45RA−, CD90+, CD49f+ hematopoietic stem cells is increased at least 2-fold, or at least 5-fold, or at least 10-fold, or at least 20-fold, or at least 30-fold, or at least or at least 40-fold, or at least 44-fold, or at least 50 fold when compared to the starting population of hematopioetic cells.

In another embodiment, the percentage of CD34+, CD45RA−, CD90+, CD49f+ hematopioetic stem cells in the total cell population following culture is at least 1%, or at least 1.5%, or at least 2%, or at least 5%, or greater. when compared to the starting population of hematopioetic cells.

In one embodiment, the starting co-culture population comprises about 300 million, or about 400 million, or about 500 million or more MLPSCs.

In one embodiment, the starting co-culture population comprises about 30 million, or about 40 million, or about 50 million or more CD34+ cells.

In one embodiment, the starting co-culture population comprises about 1.5 million, or about 2 million, or about 2.5 million or more CD34+, CD45RA−, CD90+, CD49f+ cells.

In one embodiment the HDACi is selected from the group consisting of valproic acid (VPA), trichostatin (TSA), DLS3, MS275, SAHA, and HDAC6 inhibitorl61.

In one embodiment the hematopoietic cells are also cultured in the presence of one or more growth factors elected from the group consisting of: s(SCF), GM-SCF, M-CSF, G-CSF, MGDF, EPO, FLT3-ligand, IL-1, IL-2, IL-3, IL-4, IL-6, IL-7, IL-11, TNFα or thrombopoietin.

In another embodiment the hematopoietic cells are also cultured in the presence of one or more stem cell renewal agents. The stem cell renewal agent may be, for example, SR1 or UM171.

In another embodiment the MLPSCs are isolated by immunoselection. For example, the MLPSCs may be STRO-1+ mesenchymal precursor cells or culture expanded progeny thereof. In another embodiment, the mesenchymal lineage precursor or stem cells mesenchymal stem cells or culture expanded progeny thereof.

It will be appreciated that the population of hematopoietic cells may be derived from any source including bone marrow, umbilical cord or cord blood, peripheral blood, liver, thymus, lymph, spleen or iPS cells.

In one embodiment, haematopoietic cells are added to an established adherent MLPSC cell culture. The MLPSCs may be cultured to confluence, replated and re-cultured to provide a feeder layer to which is added the hematopoietic cells for co-culturing.

The cells may be co-cultured for a period of about 2 days, or 3 days, or 4 days, or 5 days, or 6 days, or 7 days or 8 days or 9 days or 10 days or 12 days or 15 days or 20 days or longer.

The culture conditions described herein enable contact between the MLPSCs and HSCs which can facilitate transfer of a genetic payload, such as a heterologous nucleic acid or a CRISPR system, from the MLPSCs to HSCs.

Accordingly, in one embodiment the MLPSC comprise a heterologous nucleic acid molecule which is transferred to the hematopoietic stem cells having the phenotype CD34+, during culture expansion. In one embodiment the MLPSC comprise a heterologous nucleic acid molecule which is transferred to the hematopoietic stem cells having the phenotype CD34+, CD45RA−, CD90+, CD49f+ during culture expansion.

In another embodiment, CD34+, CD45RA−, CD90+, CD49f+ cells are isolated by immunoselection following culture expansion to provide an enriched population of CD34+, CD45RA−, CD90+, CD49f+ cells. This cell population may be useful for long term renewal following administration to a subject.

In another embodiment, CD34+, CD45RA−, CD90+, CD49f+ cells are removed by immunoselection following culture expansion to provide an enriched population of CD34+, CD49f− cells. This cell population may be useful for early phase neutrophil/platelet recovery following administration to a subject.

In one embodiment, the enriched population of CD34+, CD45RA−, CD90+, CD49f+ cells is subject to genetic manipulation, for example by transfection with a heterologous nucleic acid.

In one embodiment, the enriched population of CD34+, CD49f− cells is subject to genetic manipulation, for example by transfection with a heterologous nucleic acid.

The heterologous nucleic acid may be present in the form of an expression vector. Suitable expression vectors include but are not limited to plasmid, phage, autonomously replicating sequence (ARS), viral, centromere, and artificial chromosome structures. In one example the expression vector is a viral vector selected from the group consisting of Lentivirus, Baculovirus, Retrovirus, Adenovirus (AdV), Adeno-associated virus (AAV) and a recombinant form thereof.

In another embodiment the heterologous nucleic acid encodes a protein selected from the group consisting of a clotting factor, a hormone or a cytokine.

In another embodiment the heterologous nucleic acid comprises a CRISPR system or component thereof. For example, the CRISPR system may comprise a Cas expression vector and a guide nucleic acid sequence specific for an endogenous gene in the HSC. For example, the CRISPR system may comprise a Cas9 protein complexed with a guide nucleic acid sequence specific for an endogenous gene in the HSC.

In another embodiment the expression vector or CRISPR system comprises an inducible promoter.

In another embodiment the method comprises exposing the HSCs to an agent that activates the inducible promoter.

The present disclosure also provides a composition comprising HSCs obtained by a method according to the present disclosure. In one embodiment the composition obtained by a method according to the present disclosure comprises HSCs having the phenotype CD34+, CD45RA−, CD90+, CD49f+.

The present disclosure also provides a composition comprising HSCs having the phenotype CD34+, CD45RA−, CD90+, CD49f+ and MLPSCs at a respective ratio of at least 1:35, or at least 1:30, or at least 1:20, or at least 1:10, or at least 1:5, or at least 1:4.5, or at least 1:4.

The present disclosure also provides a composition comprising HSCs having the phenotype CD34+, CD45RA−, CD90+, CD49f+ and MLPSCs, wherein cells having the phenotype CD34+, CD45RA− CD90+, CD49f+ constitute at least 10% or at least 20% of the total cell population.

In one embodiment the composition further comprises a HDACi.

The present disclosure also provides a composition comprising hematopoietic stem cells having the phenotype CD34+, CD45RA−, CD90+, CD49f+, MLPSCs and a HDACI inhibitor.

In one embodiment of the composition, the HSCs comprises a heterologous nucleic acid molecule.

In another embodiment the heterologous nucleic acid encodes a protein selected from the group consisting of a clotting factor, a hormone or a cytokine.

In another embodiment the heterologous nucleic acid comprises a CRISPR system or component thereof. For example, the CRISPR system may comprise a Cas expression vector and a guide nucleic acid sequence specific for an endogenous gene in the HSC. For example, the CRISPR system may comprise a Cas9 protein complexed with a guide nucleic acid sequence specific for an endogenous gene in the HSC.

In one embodiment HSCs having the phenotype CD34+, CD45RA−, CD90+, CD49f+ constitute at least 5%, or at least 10%, or at least 20%, or at least 30% of the total number of cells in the composition.

In another embodiment the composition contains a total amount of cells of at least $10^5$ cells, at least $10^6$ cells, at least $10^7$ cells, at least $10^8$ cells or at least $10^9$ cells.

The present disclosure also provides a method of transfecting HSCs comprising culturing a population of HSCs in the presence of mesenchymal lineage precursor or stem cells (MLPSCs) and at least one histone deacetylase inhibitor (HDACi), wherein the MLPSCs comprise at least one heterologous nucleic acid molecule, and wherein the culture conditions allow for transfer of the heterologous nucleic acid molecule from the MLPSCs to the to the HSCs.

In one embodiment the HSCs have the phenotype CD34+. In another embodiment the HSCs have the phenotype CD34+, CD45RA−, CD90+, CD49f+.

The heterologous nucleic acid may be present in the form of an expression vector. Suitable expression vectors include but are not limited to plasmid, phage, autonomously replicating sequence (ARS), viral, centromere, and artificial chromosome structures. In one example the expression vector is a viral vector selected from the group consisting of Lentivirus, Baculovirus, Retrovirus, Adenovirus (AdV), Adeno-associated virus (AAV) and a recombinant form thereof.

In another embodiment the heterologous nucleic acid encodes a protein selected from the group consisting of a clotting factor, a hormone or a cytokine.

In another embodiment the heterologous nucleic acid comprises a CRISPR system or component thereof. For example, the CRISPR system may comprise a Cas expression vector and a guide nucleic acid sequence specific for an endogenous gene in the HSC. For example, the CRISPR system may comprise a Cas9 protein complexed with a guide nucleic acid sequence specific for an endogenous gene in the HSC.

In another embodiment the expression vector or CRISPR system comprises an inducible promoter.

In another embodiment the method comprises exposing the HSCs to an agent that activates the inducible promoter.

The present disclosure also provides a composition comprising an HSC which has been transfected according to a method described above.

The present disclosure also provides a method of treating a hematologic disorder in a subject in need thereof which comprises administering to the subject a composition of the present disclosure.

As used throughout, by a subject is meant an individual. Thus, subjects include, for example, domesticated animals, such as cats and dogs, livestock (e.g., cattle, horses, pigs, sheep, and goats), laboratory animals (e.g., mice, rabbits, rats, and guinea pigs), mammals, non-human mammals, primates, non-human primates, rodents, birds, reptiles, amphibians, fish, and any other animal. The subject is optionally a mammal such as a primate or a human.

In one embodiment the subject is a human. The human may be an adult or pediatric patient.

It will be appreciated that methods and compositions of the disclosure may be used in the treatment of a range of haematologic disorders.

For example, the methods and compositions of the disclosure may be used in the treatment of a disorder of platelet number and/or function such as thrombocytopenia, idiopathic thrombocytopenic purpure (ITP), or a disorder related to viral infection, drug abuse or malignancy.

In another example, the methods and compositions of the disclosure may be used in the treatment of a disorder of erythrocyte number and/or function, such as an anaemia. Examples of anaemias that may be treated include aplastic anaemia, autoimmune haemolytic anaemia, blood loss anaemia, Cooley's anaemia, Diamond-Blackfan anaemia, Fanconi anaemia, folate (folic acid) deficiency anaemia, haemolytic anaemia, iron-deficiency anaemia, pernicious anaemia, sickle cell anaemia, thalassaemia or Polycythemia Vera.

In one example, the methods and compositions of the disclosure are used in the treatment of alpha or beta thalassaemia.

In another example, the methods and compositions of the disclosure may be used in the treatment of a disorder of lymphocyte number and/or function, such as a disorder caused by a T-cell or B-cell deficiency. Examples of disorders of lymphocyte number and/or function are AIDS, leukemias, lymphomas, Hodgkins lumphoma, chronic infections such as military tuberculosis, viral infections, rheumatoid arthritis, systemic lupus erythematosus, or hereditary disorders such as agammaglobulinemia, DiGeorge anomaly, Wiskott-Aldrich syndrome, or ataxia-telangiectasia.

In another example, methods and compositions of the disclosure may be used in the treatment of a disorder of multilineage bone marrow failure, which may be the result of radiotherapy or chemotherapy or malignant replacement. For example, the disorder may be a myelofibrosis, acute myelogenous leukemia (AML), myelodysplastic syndrome (MDS), acute lymphoblastic leukemia (ALL), chromic myelogenous leukemia (CML), chronic lymphocytic leukemia (CLL)), Non-Hodgkin's lymphoma (NHL), Hodgkin's Disease (HD), multiple myeloma (MM), or a secondary malignancy disseminated to bone.

In another example, methods and compositions of the disclosure be used in the treatment of an inborn error of metabolism. For example the inborn error of metabolism are selected from the group consisting of mucopolysaccharidosis, Gaucher disease, metachromatic leukodystrophies and adrenoleukodystrophies.

The present invention is applicable to a wide range of animals. For example, the subject may be a mammal such as a human, dog, cat, horse, cow, or sheep. In one embodiment the subject is a human.

In another embodiment, the methods of the disclosure further comprise administering an immunosuppressive agent. The immunosuppressive agent may be administered for a time sufficient to permit the transplanted hematopoietic cells to be functional. The immunosuppressive agent may be selected from one or more of the following, including but not limited to corticosteroids such as prednisone, budesonide and prednisolone; calcineurin inhibitors such as cyclosporine and tacrolimus; mTOR inhibitors such as sirolimus and everolimus; IMDH inhibitors such as azathioprine, leflunomide and mycophenolate; a biologic such as abatacept, adalimumab, etanercept, infliximab or rituximab.

In one example, the immunosuppressive agent is cyclosporine. The cyclosporine may be administered at a dosage of from 5 to 40 mg/kg body wt.

DESCRIPTION OF EMBODIMENTS

General Techniques and Definitions

Figure 1:
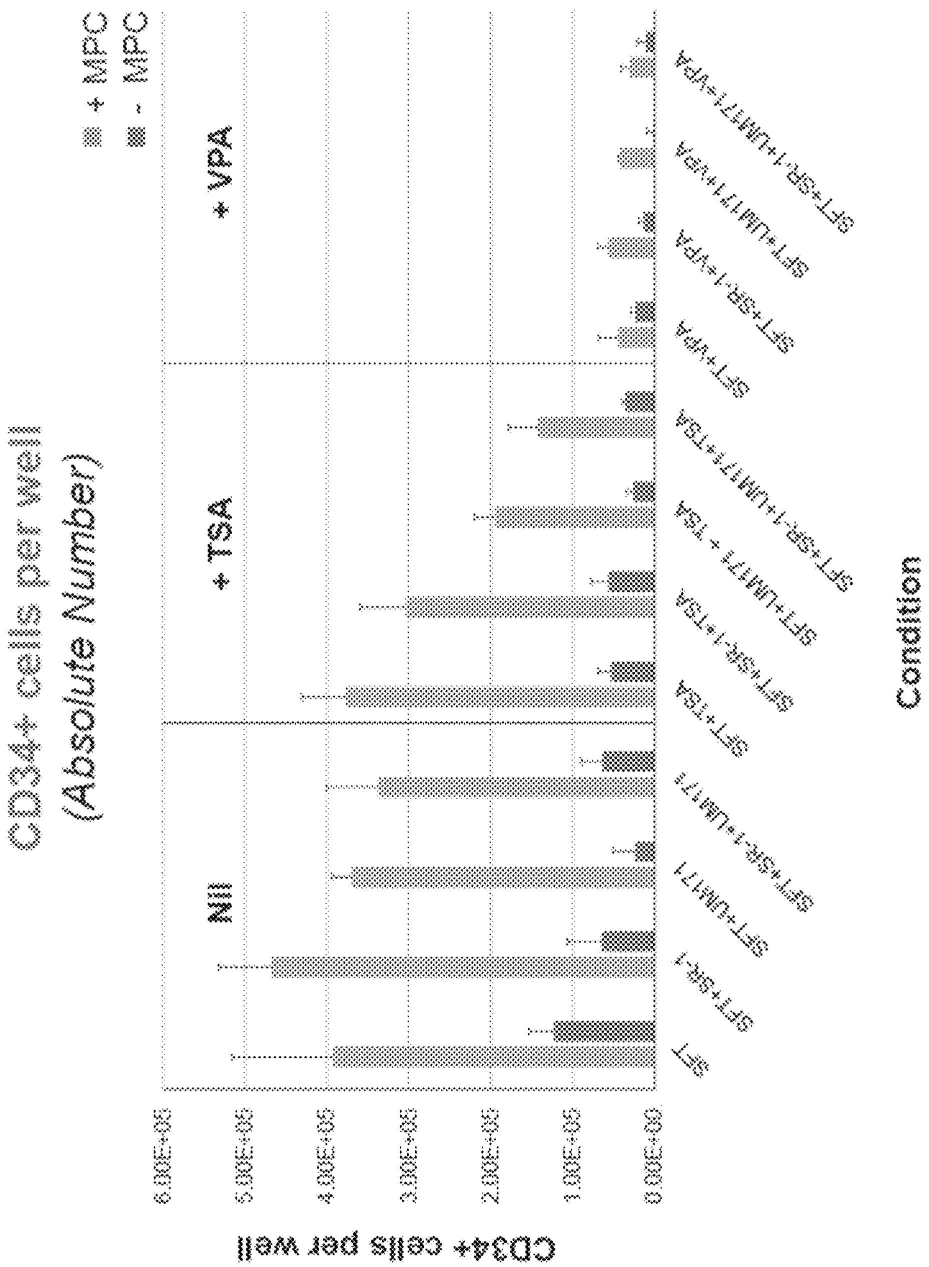
FIG. 1: Absolute number of CD34+ cells per well following 5 days in culture in the presence of absence of MPCs with (i) no HDACi; (ii) TSA or (iii) VPA.
Figure 2:
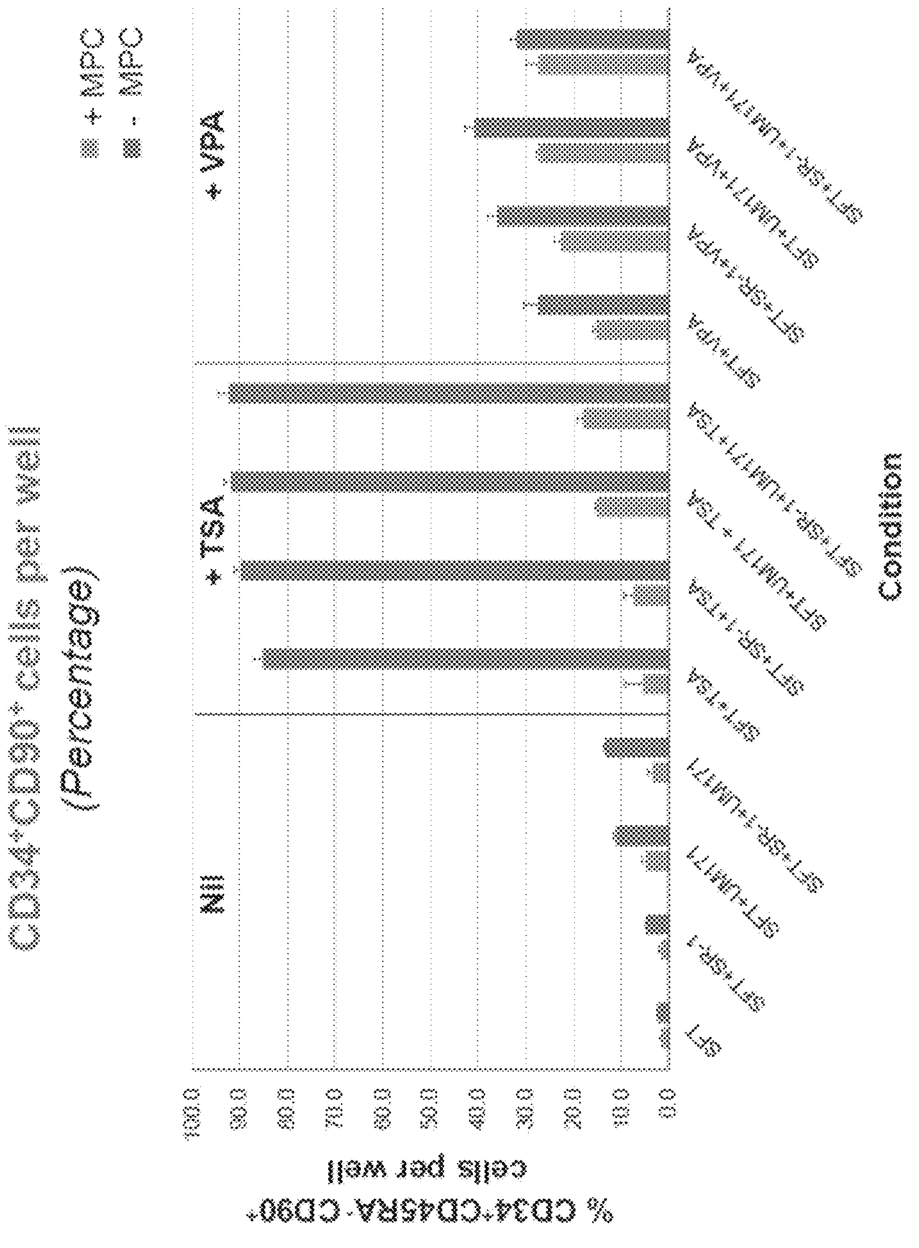
FIG. 2: Percentage of CD34+CD90+ cells per well following 5 days in culture in the presence of absence of MPCs with (i) no HDACi; (ii) TSA or (iii) VPA.
Figure 3:
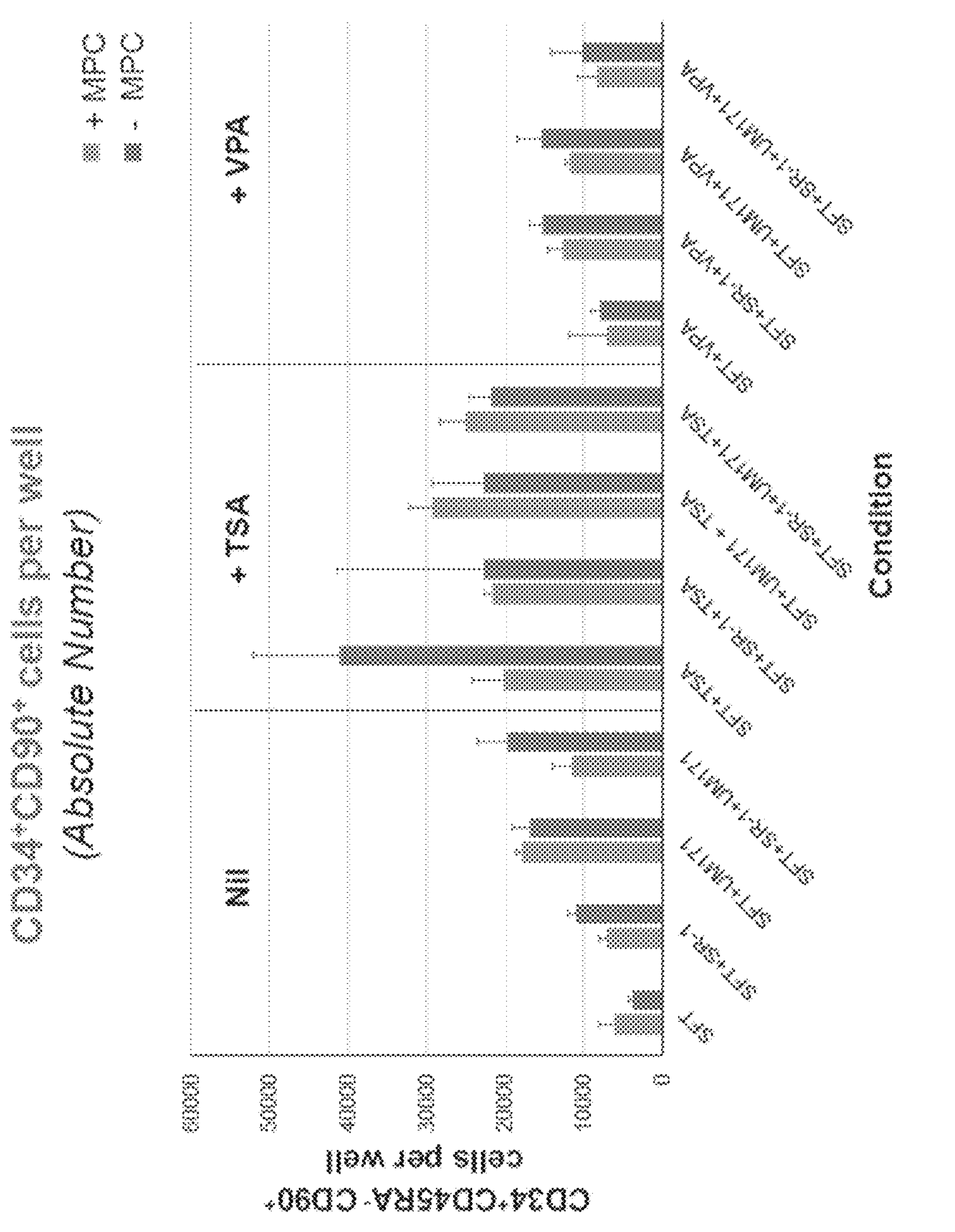
FIG. 3: Absolute number of CD34+CD90+ cells per well following 5 days in culture in the presence of absence of MPCs with (i) no HDACi; (ii) TSA or (iii) VPA.
Figure 4:
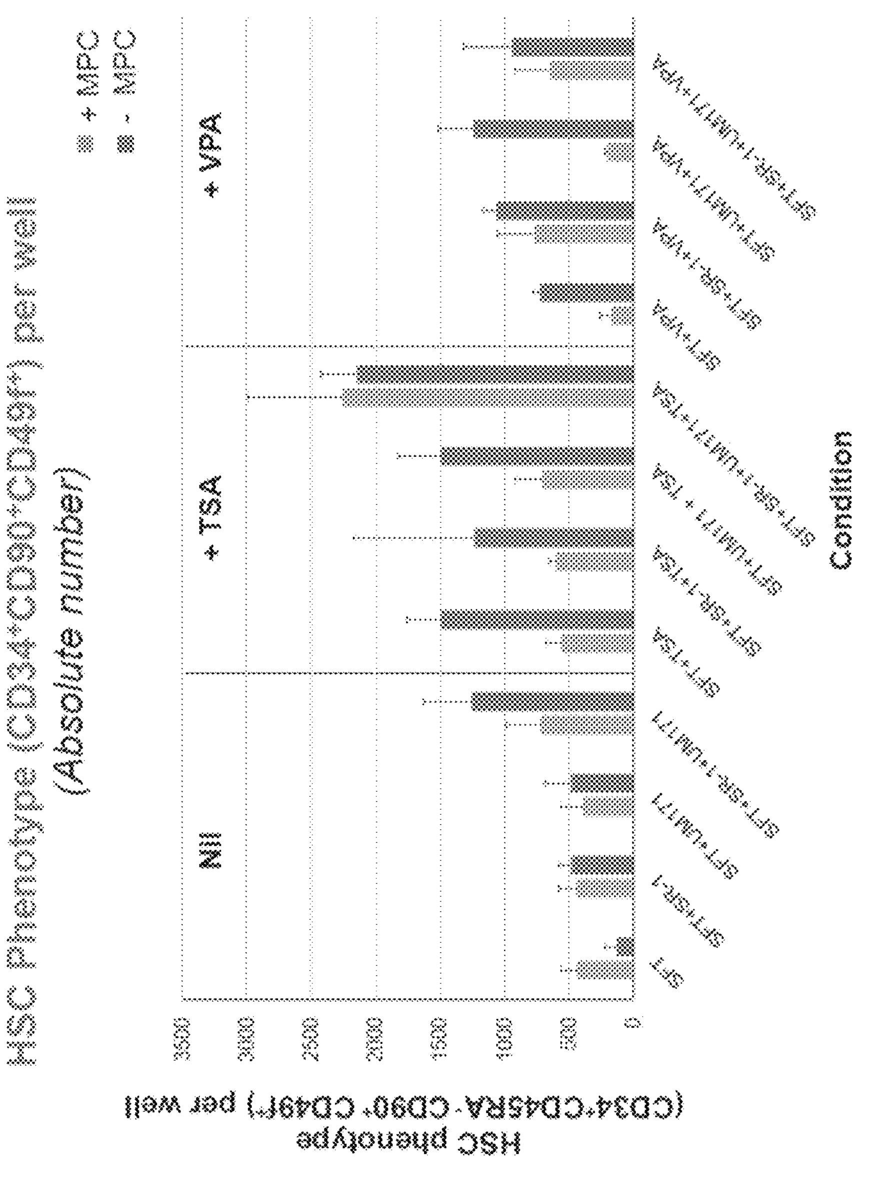
FIG. 4: Absolute number of cells exhibiting primitive HSC phenotype (CD34+CD90CD49f+) per well following 5 days in culture in the presence of absence of MPCs with (i) no HDACi; (ii) TSA or (iii) VPA.
Figure 5:
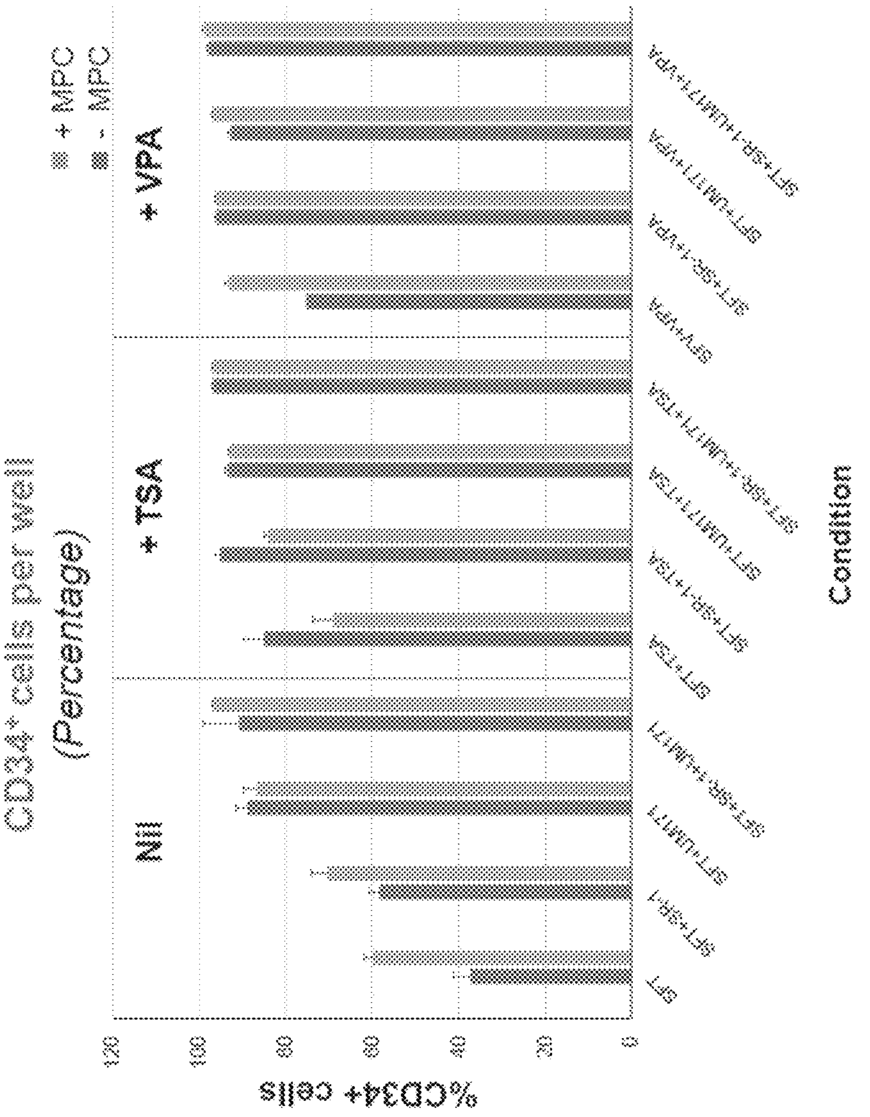
FIG. 5: Percentage of CD34+ cells per well following 10 days in culture in the presence of absence of MPCs with (i) no HDACi; (ii) TSA or (iii) VPA.
Figure 6:
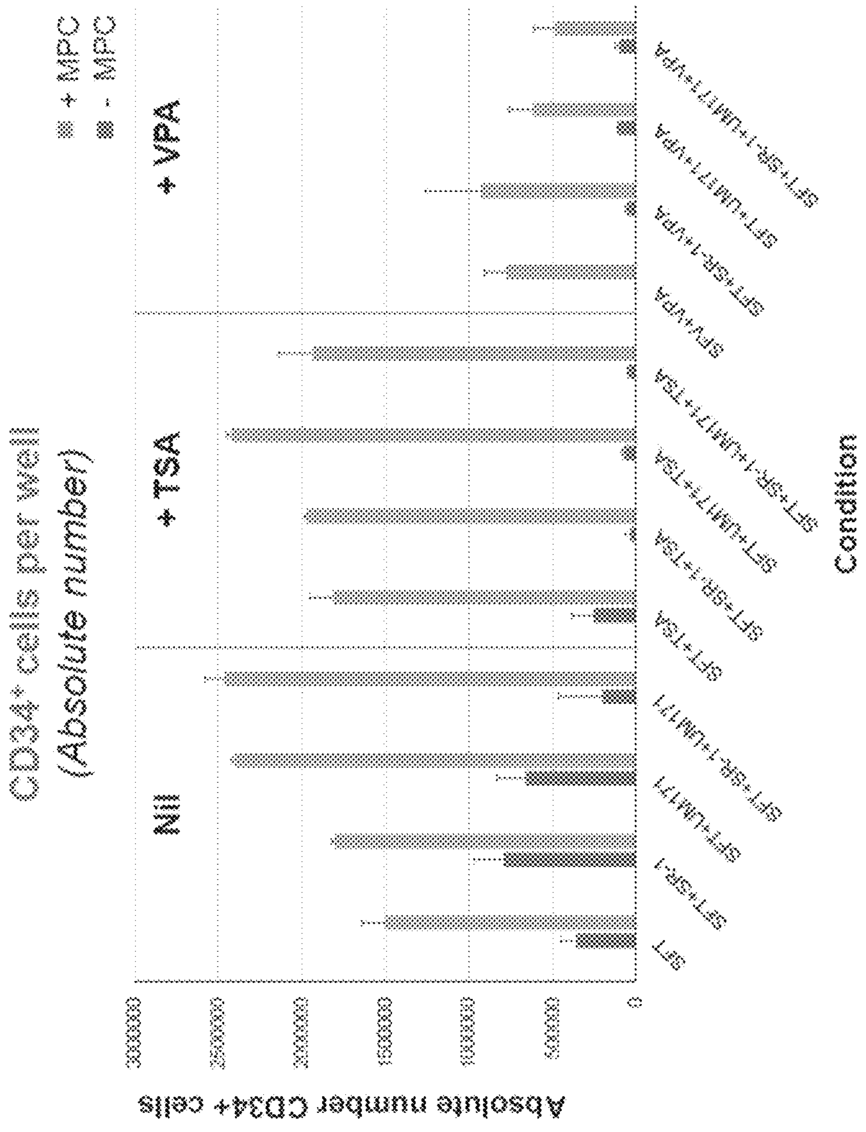
FIG. 6: Absolute number of CD34+ cells per well following 10 days in culture in the presence of absence of MPCs with (i) no HDACi; (ii) TSA or (iii) VPA.
Figure 7:
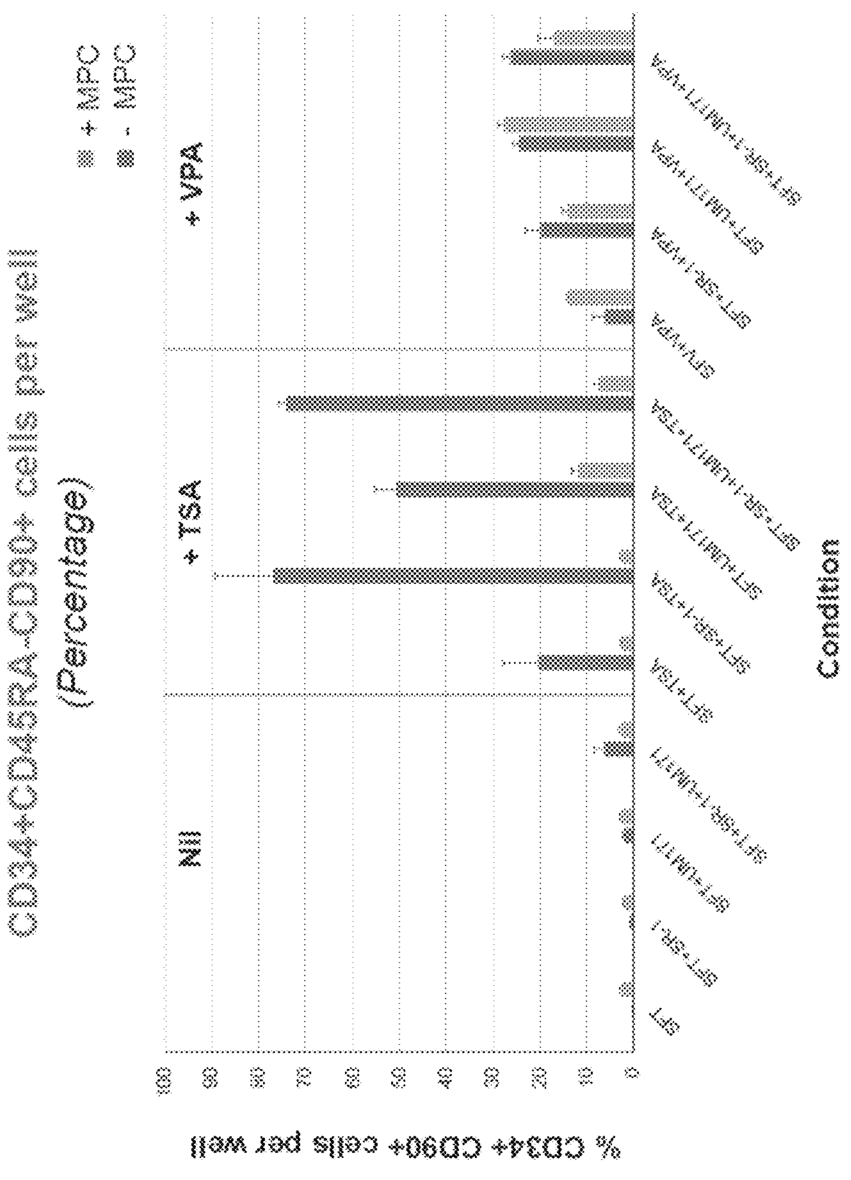
FIG. 7: Percentage of CD34+CD45RA−CD90+ cells per well following 10 days in culture in the presence of absence of MPCs with (i) no HDACi; (ii) TSA or (iii) VPA.
Figure 8:
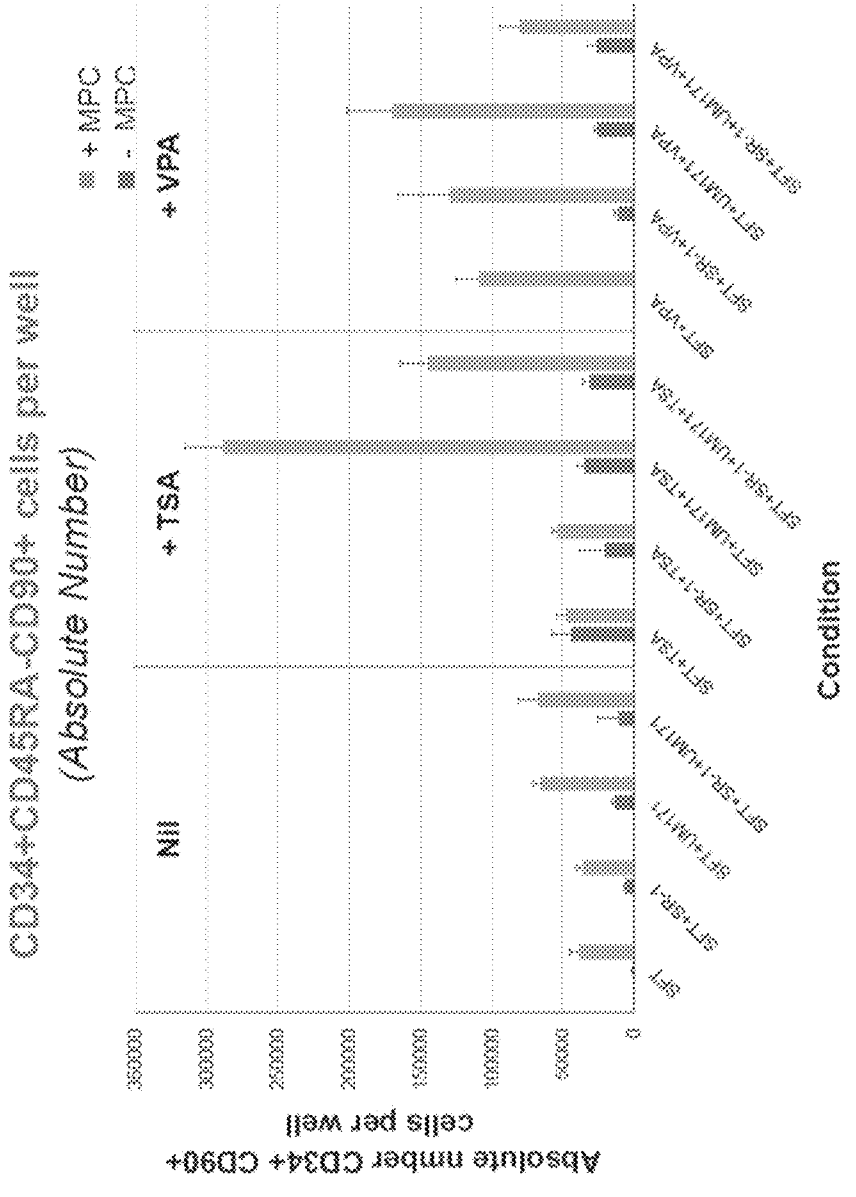
FIG. 8: Absolute number of CD34+CD45RA−CD90+ cells per well following 10 days in culture in the presence of absence of MPCs with (i) no HDACi; (ii) TSA or (iii) VPA.

Throughout this specification, unless specifically stated otherwise or the context requires otherwise, reference to a single step, composition of matter, group of steps or group of compositions of matter shall be taken to encompass one and a plurality (i.e., one or more) of those steps, compositions of matter, group of steps or group of compositions of matter.

Those skilled in the art will appreciate that the disclosure described herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific embodiments described herein, which are intended for the purpose of exemplification only. Functionally-equivalent products, compositions and methods are clearly within the scope of the disclosure.

Any example disclosed herein shall be taken to apply mutatis mutandis to any other example unless specifically stated otherwise.

Unless specifically defined otherwise, all technical and scientific terms used herein shall be taken to have the same meaning as commonly understood by one of ordinary skill in the art (e.g., in cell culture, molecular genetics, stem cell differentiation, immunology, immunohistochemistry, protein chemistry, and biochemistry).

Unless otherwise indicated, the stem cells, cell culture, and surgical techniques utilized in the present disclosure are standard procedures, well known to those skilled in the art. Such techniques are described and explained throughout the literature in sources such as Perbal, 1984; Sambrook & Green, 2012; Brown, 1991; Glover & Hames, 1995 and 1996; Ausubel., 1987 including all updates until present; Harlow & Lane, 1988; and Coligan et al., 1991 including all updates until present.

As used in this specification and the appended claims, terms in the singular and the singular forms "a," "an" and "the," for example, optionally include plural referents unless the content clearly dictates otherwise.

The term "subject" as used herein refers to a mammal including human and non-human animals. More particularly, the mammal is a human. Terms such as "subject", "patient" or "individual" are terms that can, in context, be used interchangeably in the present disclosure. In certain examples, the subject may be an adult or a child (pediatric) subject.

An "effective amount" refers to at least an amount effective, at dosages and for periods of time necessary, to achieve the desired therapeutic or prophylactic result. An effective amount can be provided in one or more administrations. In some examples of the present disclosure, the term "effective amount" is used to refer to an amount necessary to effect treatment of a disease or condition as hereinbefore described. The effective amount may vary according to the disease or condition to be treated and also according to the weight, age, racial background, sex, health and/or physical condition and other factors relevant to the mammal being treated. Typically, the effective amount will fall within a relatively broad range (e.g. a "dosage" range) that can be determined through routine trial and experimentation by a medical practitioner. The effective amount can be administered in a single dose or in a dose repeated once or several times over a treatment period.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with a disease are mitigated or eliminated.

An "hematopoietic stem cell transplantation (HSCT)" is a graft comprising multipotent hematopoietic stem cells which can be derived, for example, from bone marrow or peripheral blood. The transplant may include some non-stem cells, for example, APCs including DCs and/or lymphocytes.

The term "adult" as used herein means a human subject of 18 years of age and older.

The term "pediatric" as used herein means a human subject ranging in age from birth up to and including 17 years of age.

The term "graft" as used herein refers to a biological sample selected from bone marrow, blood (e.g. whole blood or peripheral blood mononuclear cells (PBMCs), blood products, or solid organs in which hematopoietic cells are present.

The term "allogeneic" as used herein refers to a graft (e.g. hematopoietic cells) which are donated by an individual whose genetic characteristics differ from those of the recipient, especially in regards to the major histocompatibility complex (MHC) and minor histocompatibility agents expressed on the surface of the individual's cells.

The term "autologous" as used herein refers to a graft (e.g. hematopoietic cells present in the bone marrow or peripheral blood) that uses the subject's own cells. The cells are usually harvested in advance of the subject undergoing treatment (e.g. with chemotherapy), stored and then re-infused back into the subject.

The term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−10%, more preferably +/−5%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Hematopoietic Stem Cells

"Hematopoietic stem cells" (HSCs) as used herein refer to immature blood cells having the capacity to self-renew and to differentiate into more mature blood cells comprising granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), and monocytes (e.g., monocytes, macrophages).

It is known in the art that such cells may or may not include CD34+ cells. CD34+ cells are immature cells that express the CD34 cell surface marker. CD34+ cells are believed to include a subpopulation of cells with the stem cell properties defined above. It is well known in the art that HSCs include pluripotent stem cells, multipotent stem cells (e.g., a lymphoid stem cell), and/or stem cells committed to specific hematopoietic lineages. The stem cells committed to specific hematopoietic lineages may be of T cell lineage, B cell lineage, dendritic cell lineage, Langerhans cell lineage and/or lymphoid tissue-specific macrophage cell lineage.

Human HSCs capable of long-term renewal and engraftment are considered 'primitive' in phenotype, express CD34, CD49f, and CD90. In one embodiment the primitive cells have the phenotype CD34+, CD45RA−, CD90+, CD49f+. In one embodiment they also lack expression of CD38 and any lineage-restricted antigen. In one embodiment the primitive HSCs are defined as CD34+ CD45RA− CD49f+ CD90+CD38− Lin− cells (LT-HSCs).

Mesenchymal Lineage Precursor or Stem Cells

As used herein, the term "mesenchymal lineage precursor or stem cells" refers to undifferentiated multipotent cells that have the capacity to self-renew while maintaining multipotency and the capacity to differentiate into a number of cell types either of mesenchymal origin, for example, osteoblasts, chondrocytes, adipocytes, stromal cells, fibroblasts and tendons, or non-mesodermal origin, for example, hepatocytes, neural cells and epithelial cells.

The term "mesenchymal lineage precursor or stem cells" includes both parent cells and their undifferentiated progeny. The term also includes mesenchymal precursor cells (MPC), multipotent stromal cells, mesenchymal stem cells, perivascular mesenchymal precursor cells, and their undifferentiated progeny.

Mesenchymal lineage precursor or stem cells can be autologous, allogeneic, xenogeneic, syngeneic or isogeneic. Autologous cells are isolated from the same individual to which they will be reimplanted. Allogeneic cells are isolated from a donor of the same species. Xenogeneic cells are isolated from a donor of another species. Syngeneic or isogeneic cells are isolated from genetically identical organisms, such as twins, clones, or highly inbred research animal models.

Mesenchymal lineage precursor or stem cells reside primarily in the bone marrow, but have also been shown to be present in diverse host tissues including, for example, cord blood and umbilical cord, adult peripheral blood, adipose tissue, trabecular bone and dental pulp.

Mesenchymal lineage precursor or stem cells can be isolated from host tissues and enriched for by immunoselection. For example, a bone marrow aspirate from a subject may be further treated with an antibody to STRO-1 or TNAP to enable selection of mesenchymal lineage precursor or stem cells. In one example, the mesenchymal lineage precursor or stem cells can be enriched for by using the STRO-1 antibody described in Simmons & Torok-Storb, 1991.

STRO-1+ cells are cells found in bone marrow, blood, dental pulp cells, adipose tissue, skin, spleen, pancreas, brain, kidney, liver, heart, retina, brain, hair follicles, intestine, lung, lymph node, thymus, bone, ligament, tendon, skeletal muscle, dermis, and periosteum; and are capable of differentiating into germ lines such as mesoderm and/or endoderm and/or ectoderm. Thus, STRO-1+ cells are capable of differentiating into a large number of cell types including, but not limited to, adipose, osseous, cartilaginous, elastic, muscular, and fibrous connective tissues. The specific lineage-commitment and differentiation pathway which these cells enter depends upon various influences from mechanical influences and/or endogenous bioactive factors, such as growth factors, cytokines, and/or local microenvironmental conditions established by host tissues.

The term "enriched" as used herein describes a population of cells in which the proportion of one particular cell type or the proportion of a number of particular cell types is increased when compared with an untreated population of the cells (e.g., cells in their native environment). In one example, a population enriched for STRO-1+ cells comprises at least about 0.1% or 0.5% or 1% or 2% or 5% or 10% or 15% or 20% or 25% or 30% or 50% or 75% STRO-1+ cells. In this regard, the term "population of cells enriched for STRO-1+ cells" will be taken to provide explicit support for the term "population of cells comprising X % STRO-1+ cells", wherein X % is a percentage as recited herein. The STRO-1+ cells can, in some examples, form clonogenic colonies, for example, CFU-F (fibroblasts) or a subset thereof (e.g., 50% or 60% or 70% or 70% or 90% or 95%) can have this activity.

In one example, the population of cells is enriched from a cell preparation comprising STRO-1+ cells in a selectable form. In this regard, the term "selectable form" will be understood to mean that the cells express a marker (e.g., a cell surface marker) permitting selection of the STRO-1+ cells. The marker can be STRO-1, but need not be. For example, as described and/or exemplified herein, cells (e.g., MPCs) expressing STRO-2 and/or STRO-3 (TNAP) and/or STRO-4 and/or VCAM-1 and/or CD146 and/or 3G5 also express STRO-1 (and can be STRO-$1^{bright}$). Accordingly, an indication that cells are STRO-1+ does not mean that the cells are selected by STRO-1 expression. In one example, the cells are selected based on at least STRO-3 expression, e.g., they are STRO-3+ (TNAP+).

Reference to selection of a cell or population thereof does not necessarily require selection from a specific tissue source. As described herein, STRO-1+ cells can be selected from or isolated from or enriched from a large variety of sources. That said, in some examples, these terms provide support for selection from any tissue comprising STRO-1+ cells or vascularized tissue or tissue comprising pericytes (e.g., STRO-1+ pericytes) or any one or more of the tissues recited herein.

In one example, the mesenchymal lineage precursor or stem cells of the disclosure express one or more markers individually or collectively selected from the group consisting of TNAP+, VCAM-1+, THY-1+, STRO-2+, STRO-4+ (HSP-90β), CD45+, CD146+, 3G5+.

By "individually" is meant that the disclosure encompasses the recited markers or groups of markers separately, and that, notwithstanding that individual markers or groups of markers may not be separately listed herein, the accompanying claims may define such marker or groups of markers separately and divisibly from each other.

By "collectively" is meant that the disclosure encompasses any number or combination of the recited markers or groups of markers, and that, notwithstanding that such numbers or combinations of markers or groups of markers may not be specifically listed herein, the accompanying claims may define such combinations or sub-combinations separately and divisibly from any other combination of markers or groups of markers.

A cell that is referred to as being "positive" for a given marker may express either a low (lo or dim or dull), intermediate (median) or a high (bright, bri) level of that marker depending on the degree to which the marker is present on the cell surface, where the terms relate to intensity of fluorescence or other marker used in the sorting process of the cells or flow cytometric analysis of the cells. The distinction of low (lo or dim or dull), intermediate (median), or high (bright, bri) will be understood in the context of the marker used on a particular cell population being sorted or analysed. A cell that is referred to as being "negative" for a given marker is not necessarily completely absent from that cell. This term means that the marker is expressed at a relatively very low level by that cell, and that it generates a very low signal when detectably labeled or is undetectable above background levels, for example, levels detected using an isotype control antibody.

The term "bright" or bri as used herein, refers to a marker on a cell surface that generates a relatively high signal when detectably labeled. Whilst not wishing to be limited by theory, it is proposed that "bright" cells express more of the target marker protein (for example, the antigen recognized by a STRO-1 antibody) than other cells in the sample. For instance, STRO-$1^{bri}$ cells produce a greater fluorescent signal, when labeled with a FITC-conjugated STRO-1 antibody as determined by fluorescence activated cell sorting (FACS) analysis, than non-bright cells (STRO-$1^{lo/dim/dull/intermediate/median}$). In one example, the mesenchymal lineage precursor or stem cells are isolated from bone marrow and enriched for by selection of STRO-1+ cells. In this example, "bright" cells constitute at least about 0.1% of the most brightly labeled bone marrow mononuclear cells contained in the starting sample. In other examples, "bright" cells constitute at least about 0.1%, at least about 0.5%, at least about 1%, at least about 1.5%, or at least about 2%, of the most brightly labeled bone marrow mononuclear cells contained in the starting sample. In an example, STRO-$1^{bright}$ cells have 2 log magnitude higher expression of STRO-1 surface expression relative to "background", namely cells that are STRO-1−. By comparison, STRO-$1^{lo/dim/dull}$ and/or STRO-$1^{intermediate/median}$ cells have less than 2 log magnitude higher expression of STRO-1 surface expression, typically about 1 log or less than "background".

In one example, the STRO-1+ cells are STRO-$1^{bright}$. In one example, the STRO-$1^{bright}$ cells are preferentially enriched relative to STRO-$1^{lo/dim/dull}$ or STRO-$1^{intermediate/median}$ cells.

In one example, the STRO-$1^{bright}$ cells are additionally one or more of TNAP+, VCAM-1+, THY-1+, STRO-2+, STRO-4+ (HSP-90β) and/or CD146+. For example, the cells are selected for one or more of the foregoing markers and/or shown to express one or more of the foregoing markers. In this regard, a cell shown to express a marker need not be specifically tested, rather previously enriched or isolated cells can be tested and subsequently used, isolated or enriched cells can be reasonably assumed to also express the same marker.

In one example, the STRO-$1^{bright}$ cells are perivascular mesenchymal precursor cells as defined in WO 2004/85630, characterized by the presence of the perivascular marker 3G5.

As used herein the term "TNAP" is intended to encompass all isoforms of tissue non-specific alkaline phosphatase. For example, the term encompasses the liver isoform (LAP), the bone isoform (BAP) and the kidney isoform (KAP). In one example, the TNAP is BAP. In one example, TNAP refers to a molecule which can bind the STRO-3 antibody produced by the hybridoma cell line deposited with ATCC on 19 Dec. 2005 under the provisions of the Budapest Treaty under deposit accession number PTA-7282.

Furthermore, in one example, the STRO-1+ cells are capable of giving rise to clonogenic CFU-F.

In one example, a significant proportion of the STRO-1+ cells are capable of differentiation into at least two different germ lines. Non-limiting examples of the lineages to which the cells may be committed include bone precursor cells; hepatocyte progenitors, which are multipotent for bile duct epithelial cells and hepatocytes; neural restricted cells, which can generate glial cell precursors that progress to oligodendrocytes and astrocytes; neuronal precursors that progress to neurons; precursors for cardiac muscle and cardiomyocytes, glucose-responsive insulin secreting pancreatic beta cell lines. Other lineages include, but are not limited to, odontoblasts, dentin-producing cells and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, cardiac muscle, smooth muscle, skeletal muscle, pericyte, vascular, epithelial, glial, neuronal, astrocyte and oligodendrocyte cells.

In one example, the mesenchymal lineage precursor or stem cells are mesenchymal stem cells (MSCs). The MSCs may be a homogeneous composition or may be a mixed cell population enriched in MSCs. Homogeneous MSC compositions may be obtained by culturing adherent bone marrow or periosteal cells, and the MSCs may be identified by specific cell surface markers which are identified with unique monoclonal antibodies. A method for obtaining a cell population enriched in MSCs using plastic adherence technology is described, for example, in U.S. Pat. No. 5,486,359. MSC prepared by conventional plastic adherence isolation relies on the non-specific plastic adherent properties of CFU-F. Alternative sources for MSCs include, but are not limited to, blood, skin, cord blood, muscle, fat, bone, and perichondrium.

The mesenchymal lineage precursor or stem cells may be cryopreserved prior to use.

Cryopreservation of mesenchymal lineage precursor or stem cells can be carried out using slow-rate cooling methods or 'fast' freezing protocols known in the art. Preferably, the method of cryopreservation maintains similar phenotypes, cell surface markers and growth rates of cryopreserved cells in comparison with unfrozen cells.

The cryopreserved composition may comprise a cryopreservation solution. The pH of the cryopreservation solution is typically 6.5 to 8, preferably 7.4.

The cyropreservation solution may comprise a sterile, non-pyrogenic isotonic solution such as, for example, PlasmaLyte A™. 100 mL of PlasmaLyte A™ contains 526 mg of sodium chloride, USP (NaCl); 502 mg of sodium gluconate ($C_6H_{11}NaO_7$); 368 mg of sodium acetate trihydrate, USP ($C_2H_3NaO_2 \cdot 3H_2O$); 37 mg of potassium chloride, USP (KCl); and 30 mg of magnesium chloride, USP ($MgCl_2 \cdot 6H_2O$). It contains no antimicrobial agents. The pH is adjusted with sodium hydroxide. The pH is 7.4 (6.5 to 8.0).

The cryopreservation solution may comprise Profreeze™. The cryopreservation solution may additionally or alternatively comprise culture medium.

To facilitate freezing, a cryoprotectant such as, for example, dimethylsulfoxide (DMSO), is usually added to the cryopreservation solution. Ideally, the cryoprotectant should be nontoxic for cells and patients, nonantigenic, chemically inert, provide high survival rate after thawing and allow transplantation without washing. However, the most commonly used cryoprotector, DMSO, shows some cytotoxicity. Hydroxylethyl starch (HES) may be used as a substitute or in combination with DMSO to reduce cytotoxicity of the cryopreservation solution.

The cryopreservation solution may comprise one or more of DMSO, hydroxyethyl starch, human serum components and other protein bulking agents. In one example, the cryopreserved solution comprises about 5% human serum albumin (HSA) and about 10% DMSO. The cryopreservation solution may further comprise one or more of methycellulose, polyvinyl pyrrolidone (PVP) and trehalose.

In one embodiment, cells are suspended in 42.5% Profreeze™/50% αMEM/7.5% DMSO and cooled in a controlled-rate freezer.

In a preferred embodiment of the invention, the mesenchymal lineage precursor or stem cells are obtained from a master cell bank derived from mesenchymal lineage precursor or stem cells enriched from the bone marrow of healthy volunteers. The use of mesenchymal lineage precursor or stem cells derived from such a source is particularly advantageous for subjects who do not have an appropriate family member available who can serve as the mesenchymal lineage precursor or stem cell donor, or are in need of immediate treatment and are at high risk of relapse, disease-related decline or death, during the time it takes to generate mesenchymal lineage precursor or stem cells.

The isolated or enriched mesenchymal lineage precursor or stem cells can be expanded ex vivo or in vitro by culture. As will be appreciated by those skilled in the art, the isolated or enriched mesenchymal lineage precursor or stem cells can be cryopreserved, thawed and subsequently or further expanded ex vivo or in vitro by culture.

The cultured mesenchymal lineage precursor or stem cells are phenotypically different to cells in vivo. For example, in one embodiment they express one or more of the following markers, CD44, NG2, DC146 and CD140b.

The cultured mesenchymal lineage precursor or stem cells are biologically different to cells in vivo, having a higher rate of proliferation compared to the largely non-cycling (quiescent) cells in vivo.

In one example, a population of cells enriched for mesenchymal lineage precursor or stem cells is seeded at about 6000 to 7000 viable cells/cm$^2$ in serum-supplemented culture medium, for example, Dulbecco's Modified Eagle medium (DMEM) supplemented with 10% fetal bovine serum (FBS) and 2 mM glutamine, and allowed to adhere to the culture vessel overnight at 37° C., 20% $O_2$. In an embodiment, the cells are seeded at about 6000, 6100, 6200, 6300, 6400, 6500, 6600, 6700, 6800, 6810, 6820, 6830, 6840, 6850, 6860, 6870, 6880, 6890, 6890, 6900, 6910, 6920, 6930, 6940, 6970, 6980, 6990, or 7000 viable cells/cm$^2$, preferably at about 6850 to 6860 viable cells/cm$^2$. The culture medium is subsequently replaced and the cells cultured for a total of 68 to 72 hours at 37° C., 5% $O_2$ prior to co-culturing with T cells and determining the amount of IL-2Rα expressed by the T cells.

HSC Culture Conditions

HSCs can be cultured from any cell or population of cells which contains or has the potential to develop into HSCs. In one embodiment the starting population of cells comprises at least 0.1% hematopoietic stem cells. In an embodiment, the HSCs are primary cells. Typically, primary cells are obtained directly from tissue. Methods of obtaining primary cells are well known in the art.

The starting population of hematopoietic cells may be harvested, for example, from a tissue sample of a subject or from a culture. Harvesting is defined as the dislodging or separation of cells. This is accomplished using a number of methods, such as enzymatic, non-enzymatic, centrifugal, electrical, or size-based methods, or preferably, by flushing the cells using culture media (e.g., media in which cells are incubated) or buffered solution. The cells are optionally collected, separated, and further expanded.

Conditions for culturing the starting cell population for hematopoietic stem cell expansion will vary depending, for example, on the starting cell population, the desired final number of cells, and desired final proportion of HSCs.

The cells may be co-cultured for a period of about 2 days, or 3 days, or 4 days, or 5 days, or 6 days, or 7 days or 8 days or 9 days or 10 days or 12 days or 15 days or 20 days or longer. For example, the cells may be co-cultured for at least 2 weeks, or for at least four weeks.

In one embodiment the culture medium is serum-free medium.

The expansion of HSCs may be carried out in a basal medium, which is supplemented with the mixtures of cytokines and growth factors described above. A basal medium typically comprises amino acids, carbon sources, vitamins, serum proteins (e.g. albumin), inorganic salts, divalent cations, buffers and any other element suitable for use in expansion of HSC. Examples of such basal medium appropriate for a method of expanding HSC include, without limitation, StemSpan® SFEM—Serum-Free Expansion Medium (StemCell Technologies, Vancouver, Canada), StemSpan® H3000-Defined Medium (StemCell Technologies, Vancouver, Canada), CellGro® SCGM (CellGenix, Freiburg Germany), StemPro®-34 SFM (Invitrogen).

The culture medium may comprise an effective amount of one or more additional factor(s), such as a cytokine(s). Suitable factors include insulin-like growth factor (IGF), IL-1, IL-3, IL-6, IL-11, G-CSF, GM-CSF, SCF, FLT3-L, thrombopoietin (TPO), erythropoietin, and analogs thereof. As used herein, "analogs" include any structural variants of the cytokines and growth factors having the biological activity as the naturally occurring forms, including without limitation, variants with enhanced or decreased biological activity when compared to the naturally occurring forms or cytokine receptor agonists such as an agonist antibody against the TPO receptor (for example, VB22B sc(Fv)2 as detailed in patent publication WO 2007/145227, and the like). Cytokine and growth factor combinations are chosen to expand HSC and progenitor cells while limiting the production of terminally differentiated cells. In one specific embodiment, one or more cytokines and growth factors are selected from the group consisting of SCF, Flt3-L and TPO. In one specific embodiment, at least TPO is used in a serum-free medium under suitable conditions for HSC expansion.

Human IL6 or interleukin-6, also known as B-cell stimulatory factor 2 has been described by (Kishimoto, Ann. review of 1 mm. 23:1 2005) and is commercially available. Human SCF or stem cell factor, also known as c-kit ligand, mast cell growth factor or Steel factor has been described (Smith, M A et al., ACTA Haematologica, 105, 3:143, 2001) and is commercially available. Flt3-L or FLT-3 Ligand, also referred as FL is a factor that binds to flt3-receptor. It has been described (Hannum C, Nature 368 (6472): 643-8) and is commercially available. TPO or thrombopoietin, also known as megakarayocyte growth factor (MGDF) or c-Mpl ligand has been described (Kaushansky K (2006). N. Engl. J. Med. 354 (19): 2034-45) and is commercially available.

Compositions and Administration

A composition comprising HSCs may be prepared in a pharmaceutically acceptable carrier. The term "pharmaceutically acceptable carrier" as used herein refers to compositions of matter that facilitate the storage, administration, and/or maintain the biological activity of the mesenchymal lineage precursor or stem cells.

In one example, the carrier does not produce significant local or systemic adverse effect in the recipient. The pharmaceutically acceptable carrier may be solid or liquid. Useful examples of pharmaceutically acceptable carriers include, but are not limited to, diluents, solvents, surfactants, excipients, suspending agents, buffering agents, lubricating agents, adjuvants, vehicles, emulsifiers, absorbants, dispersion media, coatings, stabilizers, protective colloids, adhesives, thickeners, thixotropic agents, penetration agents, sequestering agents, scaffolds, isotonic and absorption delaying agents that do not affect the viability and activity of the mesenchymal lineage precursor or stem cells. The selection of a suitable carrier is within the skill of those skilled in the art.

Compositions of the disclosure may conveniently be presented in unit dosage form and may be prepared by any of the methods well known in the art. The term "dosage unit form" as used herein refers to physically discrete units suited as unitary dosages for subjects to be treated; each unit containing a predetermined quantity of active compound calculated to produce the desired therapeutic or prophylactic effect in association with the pharmaceutical carrier. The dose of mesenchymal lineage precursor or stem cells may vary according to factors such as the disease state, age, sex, and weight of the subject to be treated.

Exemplary doses include at least about $1\times10^6$ cells. For example, a dose can comprise between about $1.0\times10^6$ to about $1\times10^{10}$ cells, for example, between about $1.1\times10^6$ to about $1\times10^9$ cells, for example, between about $1.2\times10^6$ to about $1\times10^8$ cells, for example, between about $1.3\times10^6$ to about $1\times10^7$ cells, for example, between about $1.4\times10^6$ to about $9\times10^6$ cells, for example, between about $1.5\times10^6$ to about $8\times10^6$ cells, for example, between about $1.6\times10^6$ to about $7\times10^6$ cells, for example, between about $1.7\times10^6$ to about $6\times10^6$ cells, for example, between about $1.8\times10^6$ to about $5\times10^6$ cells, for example, between about $1.9\times10^6$ to about $4\times10^6$ cells, for example, between about $2\times10^6$ to about $3\times10^6$ cells.

In one example, the dose comprises between about $5\times10^5$ to $2\times10^7$ cells, for example, between about $6\times10^6$ cells to about $1.8\times10^7$ cells. The dose may be, for example, about $6\times10^6$ cells or about $1.8\times10^7$ cells.

The HSCs comprise at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the cell population of the composition.

Compositions of the disclosure can be administered by a route that is suitable for the particular disease state to be treated. For example, compositions of the disclosure can be administered systemically, i.e., parenterally, intravenously or by injection. Compositions of the disclosure can be targeted to a particular tissue or organ.

Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In some embodiments, it may not be necessary or desirable to immunosuppress a patient prior to initiation of therapy with cellular compositions. This may be accomplished through the use of systemic or local immunosuppressive agents, or it may be accomplished by delivering the cells in an encapsulated device. The cells may be encapsulated in a capsule that is permeable to nutrients and oxygen required by the cell and therapeutic factors the cell is yet impermeable to immune humoral factors and cells. Preferably the encapsulant is hypoallergenic, is easily and stably situated in a target tissue, and provides added protection to the implanted structure. These and other means for reducing or eliminating an immune response to the transplanted cells are known in the art. As an alternative, the cells may be genetically modified to reduce their immunogenicity.

It will be appreciated that the HSCs may be administered with other beneficial drugs or biological molecules (growth factors, trophic factors). When administered with other agents, they may be administered together in a single pharmaceutical composition, or in separate pharmaceutical compositions, simultaneously or sequentially with the other agents (either before or after administration of the other agents). Bioactive factors which may be co-administered include anti-apoptotic agents (e.g., EPO, EPO mimetibody, TPO, IGF-I and IGF-II, HGF, caspase inhibitors); anti-inflammatory agents (e.g., p38 MAPK inhibitors, TGF-beta inhibitors, statins, IL-6 and IL-1 inhibitors, PEMIROLAST™, TRANILAST™, REMICADE™, SIROLIMUS™, and non-steroidal anti-inflammatory drugs (NSAIDs) such as TEPDXALIN™, TOLMETIN™, SUPROFEN™); immunosupressive/immunomodulatory agents (e.g., calcineurin inhibitors such as cyclosporine, tacrolimus); mTOR inhibitors (e.g., SIROLIMUS™, EVEROLIMUS™); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., anti-thymocyte globulin (ATG); anti-lymphocyte globulin (ALG); monoclonal anti-T cell antibody OKT3)); anti-thrombogenic agents (e.g., heparin, heparin derivatives, urokinase, PPack (dextrophenylalanine proline arginine chloromethylketone), antithrombin compounds, platelet receptor antagonists, anti-thrombin antibodies, anti-platelet receptor antibodies, aspirin, dipyridamole, protamine, hirudin, prostaglandin inhibitors, and platelet inhibitors); and anti-oxidants (e.g., probucol, vitamin A, ascorbic acid, tocopherol, coenzyme Q-10, glutathione, L-cysteine, N-acetylcysteine) as well as local anesthetics.

Genetically-Modified Cells

In one embodiment, the HSCs or MLPSCs are genetically modified, for example, to express and/or secrete a protein of interest, for example, a protein providing a therapeutic and/or prophylactic benefit.

The term "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (cDNA) which may be isolated from natural sources, recombinantly produced, or artificially synthesized. A further example of a polynucleotide is polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as nucleotide polymers.

HSCs or MLPSCs of the present disclosure can be modified to introduce an above referenced nucleic acid. The term "introduced" is used in the context of the present disclosure to refer to the introduction of a nucleic acid into the nucleus or cytoplasm of a mesenchymal lineage precursor or stem cell according to the present disclosure.

HSCs or MLPSCs are considered "modified" when a nucleic acid has been transferred into the cell by any suitable means of artificial manipulation, or where the cell is a progeny of an originally altered cell that has inherited a nucleic acid.

Terms such as "genetically altered", "transfected", "transduced" or "genetically transformed" can also be used interchangeably in the context of the present disclosure to refer to modified mesenchymal lineage precursor or stem cells. HSCs or MLPSCs can be modified in a stable or transient fashion.

In an example, HSCs or MLPSCs can be modified to introduce a vector expressing a nucleic acid. Numerous vectors for expression in cells are known in the art. Vector components generally include, but are not limited to, one or more of the following: a signal sequence, a sequence encoding a nucleic acid such as an oligonucleotide, an enhancer element, a promoter, and a transcription termination sequence.

Exemplary expression vectors include plasmid, phage, autonomously replicating sequence (ARS), viral, centromere, artificial chromosome, chromosome, or other structure able to express a nucleic acid in a mesenchymal lineage precursor or stem cell according to the present disclosure.

Suitable vector plasmids for transfecting into mesenchymal lineage precursor or stem cells include lipid/DNA complexes, such as those described in U.S. Pat. Nos. 5,578,475; 6,020,202; and 6,051,429. Suitable reagents for making DNA-lipid complexes include lipofectamine (Gibco/Life Technologies #11668019) and FuGENE™ 6 (Roche Diagnostics Corp. #1814443); and LipoTAXI™ (Invitrogen Corp., #204110).

In another example, HSCs or MLPSCs are modified to introduce a nucleic acid using a viral expression vector. Exemplary viral expression vectors include Lentivirus, Baculovirus, Retrovirus, Adenovirus (AdV), Adeno-associated virus (AAV) including recombinant forms such as recombinant adeno-associated virus (rAAV) and derivatives thereof such as self-complementary AAV (scAAV) and non-integrating AV.

In an example, the viral vector is replication-defective. In this example, replication genes are deleted or replaced with an expression cassette with a high activity promoter. For example, in the context of AV, E1/E3 genes can be deleted or replaced. In the context of AAV, E1A and E1B genes can be deleted or replaced. Exemplary high activity promoters include CMV, EF1a, SV40, PGK1, Ubc, human beta actin, CAG, TRE, UAS and Ac5.

In an example, HSCs or MLPSCs are modified to introduce a nucleic acid using an AV vector or a recombinant form thereof. Various AV serotypes may be suitable for modifying cells to introduce the nucleic acid. In an example, AV serotype 1 (AV1) is used to modify mesenchymal lineage precursor or stem cells. In another example, AV2 is used to modify mesenchymal lineage precursor or stem cells. In other examples, AV3, AV4, AV7, AV8, AV9, AV10, AV11, AV12 or AV13 is used to modify HSCs or MLPSCs. In another example, AV5 is used to modify HSCs or MLPSCs. In another example, AV6 is used to modify mesenchymal lineage precursor or stem cells.

In an example, HSCs or MLPSCs are modified to introduce a nucleic acid using an AAV vector or a recombinant form thereof. Various AAV serotypes may also be suitable for modifying HSCs or MLPSCs.

In an example, AAV serotype 1 (AAV1) is used to modify HSCs or MLPSCs. In another example, AAV2 is used to modify HSCs or MLPSCs. In other examples, AAV3, AAV4, AAV7, AAV8, AAV9, AAV10, AAV11, AAV12 or AAV13 is used to modify HSCs or MLPSCs. In another example, AAV5 is used to modify HSCs or MLPSCs. In another example, AAV6 is used to modify HSCs or MLPSCs.

The optimal vector can be identified using various techniques known in the art. In an example, mesenchymal lineage precursor or stem cells can be contacted/transfected with various vectors expressing green fluorescent protein (GFP). In this example, optimal vectors can be identified based on transfection/transduction efficiency, GFP expression level, cellular tropism, and/or persistence of GFP expression.

Methods of viral transduction are known in the art (e.g. U.S. Pat. Nos. 6,723,561; 6,627,442). Various viral expression vector systems are also available from commercial suppliers such as Miltenyi Biotech (MACSductin), Sigma-Aldrich (ExpressMag) and Thermo Fisher Scientific (ViraPower).

Efficiencies of modification are rarely 100%, and it is usually desirable to enrich the population for cells that have been successfully modified. In an example, modified cells can be enriched by taking advantage of a functional feature of the new genotype. One exemplary method of enriching modified cells is positive selection using resistance to a drug such as neomycin.

Delivery to Co-Cultured HSCs

In one example, the present disclosure encompasses methods of delivering a nucleic acid to HSCs by contacting them through co-culture with MLPSCs that have been modified to comprise a heterologous nucleic acid or vector expressing the same. For the avoidance of doubt the nucleic acid being delivered to a HSC cell is the nucleic acid introduced to the modified mesenchymal lineage precursor or stem cell.

Transfer of the nucleic acid may occur via direct or indirect contact between the MLPSCs and HSCs. "Direct contact" is used in the context of the present disclosure to refer to physical contact between the HSC and a modified MLPSC that facilitates transfer of a nucleic acid. For example, a target cell and a modified MLPSC can be in direct contact via a common connexin (i.e. a connexin that is expressed by both the HSC and the modified mesenchymal lineage precursor or stem cell). In this example, the common connexin facilitates transfer of the nucleic acid from the MLPSC to the HSC via a gap junction. In an example, the gap junction is formed by Cx40. In another example, the gap junction is formed by Cx43. In another example, the gap junction is formed Cx45, Cx32 and/or Cx37.

"Indirect contact" is used in the context of the present disclosure to refer to delivery of a nucleic acid from a MLPSC to a HSC without direct contact. For example, a modified MLPSC in close proximity to a target cell may be in indirect contact with the target cell. In an example, a modified MLPSC in indirect contact with an HSC can deliver a nucleic acid to the target cell via exosomes.

In another example, a modified MLPSC in direct contact with HSCs can deliver a nucleic acid to the target cell via a common connexin and indirectly via exosomes.

In another example, the HSC has a common connexin with the modified MLPSC. In an example, the HSC expresses Cx40. In another example, the HSC expresses Cx43. In another example, a target cell expresses Cx45, Cx32 and/or Cx37.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

EXAMPLES

Example 1: Immunoselection of Mesenchymal Lineage Precursor or Stem Cells (MLPSCs)

Bone marrow (BM) was harvested from healthy normal adult volunteers (20-35 years old). Briefly, 40 ml of BM is aspirated from the posterior iliac crest into lithium-heparin anticoagulant-containing tubes.

Bone marrow mononuclear cells (BMMNC) were prepared by density gradient separation using Lymphoprep™ (Nycomed Pharma, Oslo, Norway) as previously described by Zannettino et al., 1998. Following centrifugation at 400×g for 30 minutes at 4° C., the buffy layer is removed with a transfer pipette and washed three times in "HHF", composed of Hank's balanced salt solution (HBSS; Life Technologies, Gaithersburg, MD), containing 5% fetal calf serum (FCS, CSL Limited, Victoria, Australia).

STRO-3+ (or TNAP+) cells were subsequently isolated by magnetic activated cell sorting as previously described by Gronthos & Simmons, 1995; and Gronthos, 2003. Briefly, approximately 1-3×$10^8$ BMMNC are incubated in blocking buffer, consisting of 10% (v/v) normal rabbit serum in HHF for 20 minutes on ice. The cells are incubated with 200 µl of a 10 µg/ml solution of STRO-3 mAb in blocking buffer for 1 hour on ice. The cells are subsequently washed twice in HHF by centrifugation at 400×g. A 1/50 dilution of goat anti-mouse γ-biotin (Southern Biotechnology Associates, Birmingham, UK) in HHF buffer is added and the cells incubated for 1 hour on ice. Cells are washed twice in MACS buffer ($Ca^{2+}$- and $Mg^{2+}$-free PBS supplemented with 1% BSA, 5 mM EDTA and 0.01% sodium azide) as above and resuspended in a final volume of 0.9 ml MACS buffer.

One hundred µl streptavidin microbeads (Miltenyi Biotec; Bergisch Gladbach, Germany) are added to the cell suspension and incubated on ice for 15 min. The cell suspension is washed twice and resuspended in 0.5 ml of MACS buffer and subsequently loaded onto a mini MACS column (MS Columns, Miltenyi Biotec), and washed three times with 0.5 ml MACS buffer to retrieve the cells which did not bind the STRO-3 mAb (deposited on 19 Dec. 2005 with American Type Culture Collection (ATCC) under accession number PTA-7282—see International publication WO 2006/108229). After addition of a further 1 ml MACS buffer, the column is removed from the magnet and the TNAP+ cells are isolated by positive pressure. An aliquot of cells from each fraction can be stained with streptavidin-FITC and the purity assessed by flow cytometry.

Example 2: Co-Culture of HSCs and Mesenchymal Lineage Precursor or Stem Cells (MLPSCs)

Cells: CB CD34+ (Stem Cell Technologies)

Medium: StemSpan SFEM (StemCell Technologies) supplemented with:
- Human low density lipoprotein (Stem Cell Technologies) 10 µg/ml
- Growth Factors ('SFT'):
- rHu-SCF 100 ng/ml
- rHu-FLT3Ligand 100 ng/ml
- rHu-TPO 50 ng/ml
- (All recombinant cytokines are from R&D Systems)

Small Molecules:
- SR1 (500 nM); UM171 (35 nM); Trichostatin A (TSA, 50 nM); Valproic Acid (VPA, 500 µM) (all from Stem Cell Technologies)

Assay conditions:
- Day −1 MPC (MCBCC006) plated at 50,000/well in 2×24-well plates in Alpha-MEM/10% FBS
- Day 0 10,000 CD34+ cells per well plated into each well of two 24 well plates. MPC containing wells were first washed to remove FBS medium.
- The remaining CD34+ cells were cultured at the same concentration in a T-25 flask in StemSpan/SFT/SR-1+ UM171. This was to provide bulk cells for set up of flow cytometry analysis and to define electronic compensation settings for multicolour analysis.
- Day 3 All groups were fed by removing 1.5 mL of media and replacing with 2.0 mL of fresh media+ additives.
- Day 5 Flow cytometric analysis: 1.5 mL of culture media was harvested from each well. For the suspension (No MPG) groups this was achieved by first aspirating the medium up and down to completely suspend the CD34+ cells before removing 1.5 mL of the suspension. For the +MPG groups, the CD34+ cells were resuspended in such a way that the MPC feeder layer was left intact. After the cells were removed from each well, they were replaced with 2.0 mL of fresh media+additives. A cell count was performed on all wells. This was required to determine not only the incidence of populations identified by FACS analysis, but also their absolute number.
- Day 8 All groups were fed by removing 2.0 mL of media and replacing with 2.0 mL of fresh media and additives.

Day 10 Flow cytometric analysis: The complete content of each well was harvested. For the suspension (No MPG) groups this was achieved by first aspirating the medium up and down to completely suspend the CD34+ cells before removing the suspension. For the +MPG groups, the CD34+ cells in suspension were first harvested (as described above for Day 5). CD34+ cells attached to the MPC layer were then detached by a brief exposure (5 mins) to 0.05% trypsin-EDTA in PBS at 37° C., the trypsin quenched in 10% FBS and the detached cells pooled with the previously harvested suspension fraction to represent the Day 10 harvest.

Flow Cytometric Analysis:

A 4-colour flow cytometric analysis was performed to allow identification and quantitation of CD34+ cells and relevant subpopulations including candidate hematopoietic stem cells (HSC) according to the phenotype CD34+ CD45RA−CD90+CD49f+ described for cord blood (Notta et al., (2011) Science 333: 218-221). All antibody conjugates were used at concentrations recommended by the manufacturers.

As noted above, the bulk culture of CD34+ cells in StemSpan/SFT/SR-1+ UM171 was used at both Day 5 and Day 10 to establish settings for flow cytometric analysis and to establish compensation settings. Stains with the following antibody/antibody combinations were performed:

1. Cells alone
2. PE-Cy7/FITC/PE/APC isotypes (pool)
3. CD34-PECy7
4. CD45RA−FITC
5. CD90-PE
6. CD49f-APC
7. CD34-PECy7/CD45RA−FITC/IgG1-PE Isotype/CD49f-APC
8. CD34-PECy7/CD45RA−FITC/CD90-PE/Rat IgG2a isotype-APC
9. CD34-PECy7/CD45RA−FITC/CD90-PE/CD49f-APC Each group was stained with the 4 colour panel (9).

Results

Cord blood derived CD34+ HSCs were cultured in the presence and absence of immunoselected MPCs in the presence of:

SFT
SFT+VPA
SFT+SR-1
SFT+SR-1+UM171
SFT+UM171
SFT+SR-1+TSA
SFT+TSA
SFT+SR-1+VPA:
SFT+UM171+TSA
SFT+UM171+VPA
SFT+SR-1+UM171+TSA
SFT+SR-1+UM171+VPA.

Results showing numbers of CD34+ cells and of various subsets including the candidate HSC phenotype (CD34+ CD45RA−CD90+CD49f+) at day 5 of culture are shown in FIGS. 1 to 4, and at day 10 of culture in FIGS. 5 to 9. Results of flow cytometric analysis at day 10 of culture are shown in FIG. 10.

Figure 9:
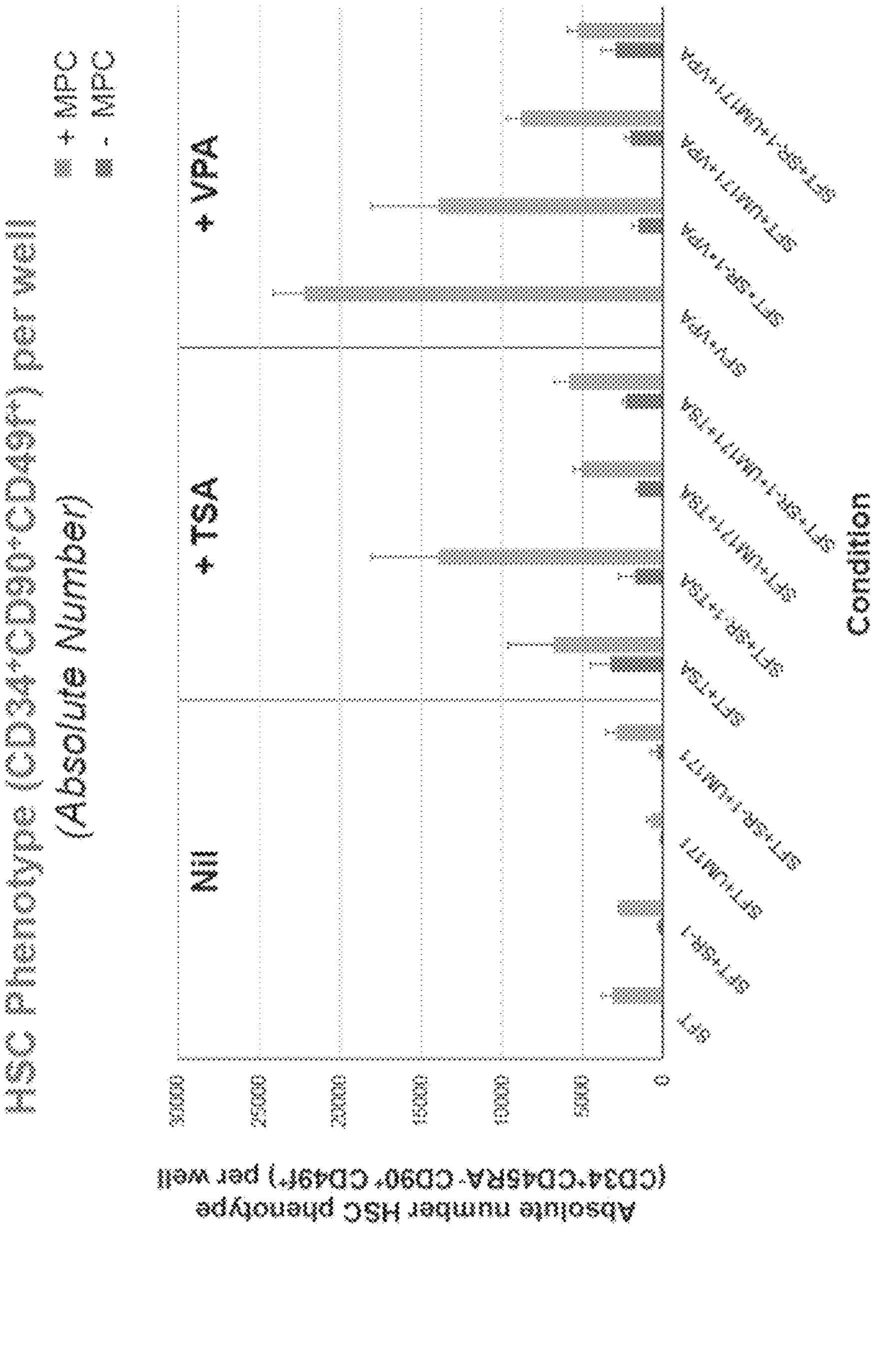
FIG. 9: Absolute number of cells exhibiting primitive HSC phenotype (CD34+CD90CD49f+) per well following 10 days in culture in the presence of absence of MPCs with (i) no HDACi; (ii) TSA or (iii) VPA.

FIG. 9 shows that the presence of MPCs and an HDACi (either TSA or VPA) results in substantially greater expansion of CD34+ cells with the primitive HSC phenotype CD34+CD45RA−CD90+CD49f+ than in the absence of MPCs or a HDACi.

Figure 10:
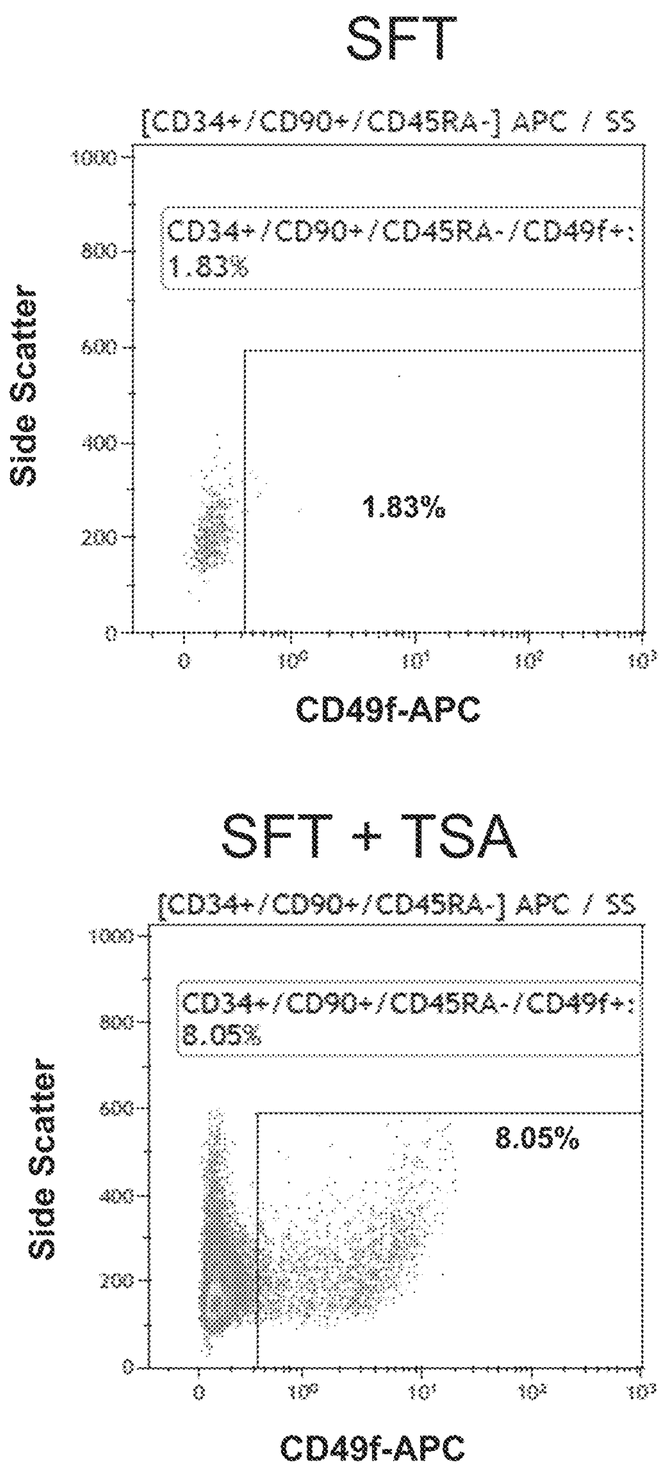
FIG. 10: Flow cytometric analysis of cells exhibiting primitive HSC phenotype (CD34+CD90CD49f+) per well following 10 days in culture in the presence of absence of MPCs with (i) no HDACi; (ii) TSA or (iii) VPA.
Figure 10:
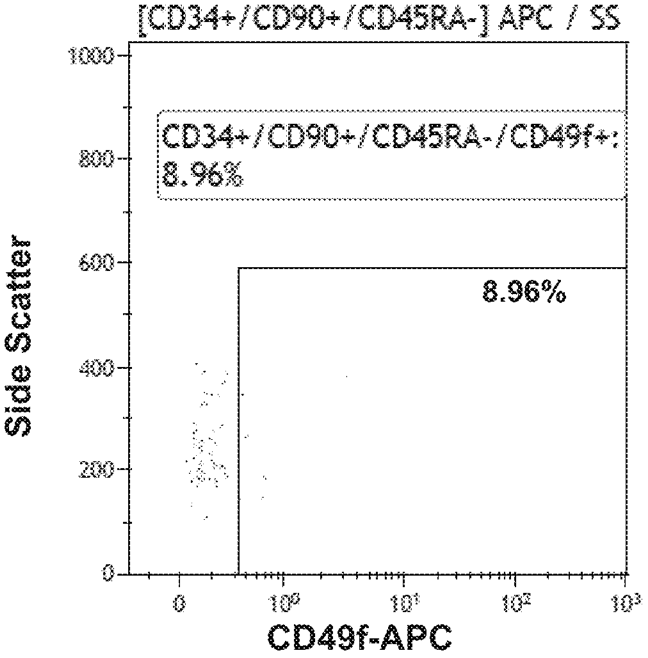
Figure 10:
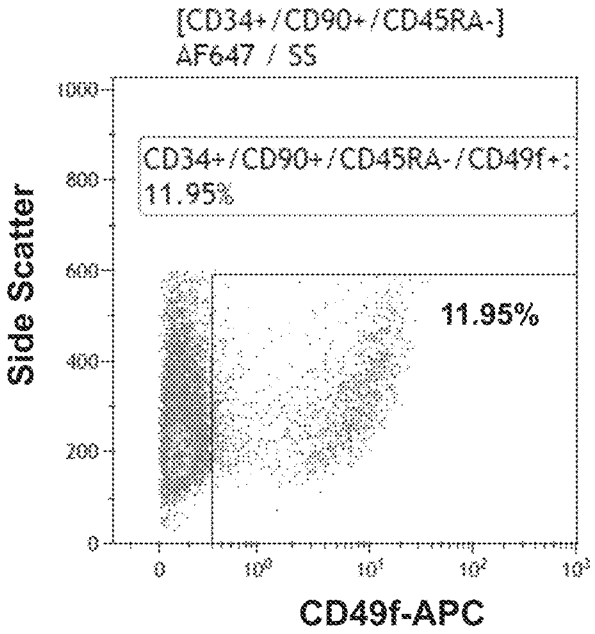
Figure 10:
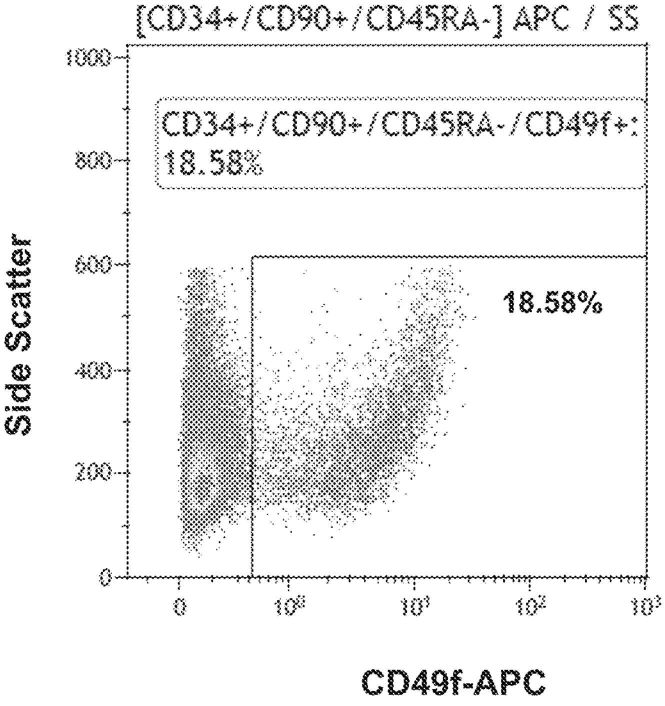
Figure 10:
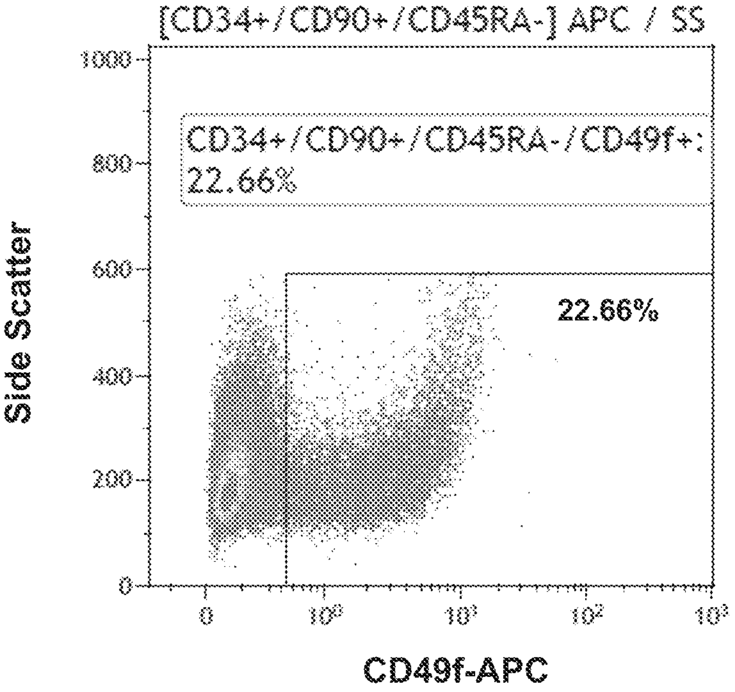

FIG. 10 shows that co-culture of CD34+ cells with MPCs markedly synergises with HDACi to enhance generation of HSCs with the primitive phenotype CD34+CD45RA−CD90+CD49f+.

These results show a substantial increase in primitive HSCs in particular during culture. For example, the starting population of co-cultured cells comprises about 100,000 MPCs and about 10,000 CD34+ cells. Of those 10,000 CD34+ cells, about 500 have the primitive phenotype CD34+CD45RA−CD90+CD49f+. After 10 days in co-culture with MPCs, SFV and VPA, for example, the number of CD34+ cells had increased to about 800,000 and the number of CD34+CD45RA−CD90+CD49f+ cells had increased to about 22,000 cells. This represents about a 44-fold increase in the number of CD4+CD90+CD49f+ cells over a 10 day period.

Over the 10 day period the number of MPCs in culture remained constant (at about 100,000 cells). The ratio of CD34+CD45RA−CD90+CD49f+ cells: MPCs therefore increased over the 10 day period from 1:200 to 1:4.5.

For comparison, state of the art methods for expanding CD34+ cells prior to this disclosure involved culturing CD34+ cells in the presence of SFT, SR-1 and UM171 and in the absence of MPCs (Boitano et al (2010) Science 329: 1345-1348; Fares et al (2014) Science 345: 1509-1512). As shown in FIG. 9, the number of CD34+CD45RA−CD90+ CD49f+ cells present after a 10 day culture period under these conditions was very low (less than about 800 cells).

Figure 11:
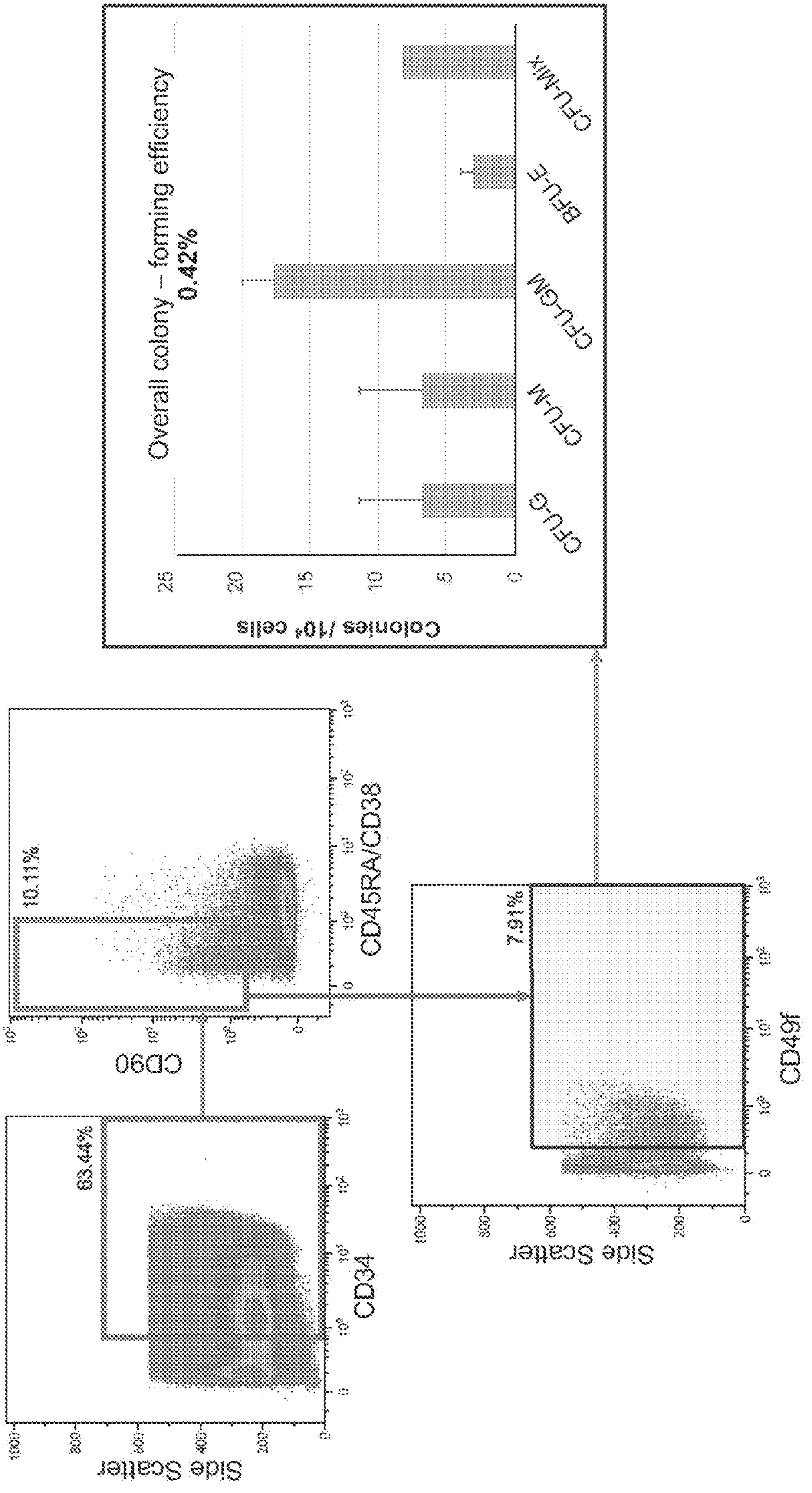
FIG. 11: CD34+CD38−CD45RA−CD90+CD49f+ cells isolated by FACS were cultured in MethoCult™ H4435 Enriched (Stem cell Technologies), and tested for colony forming efficiency on day 14 of culture. Overall colony forming efficiency was 0.42%.

CD34+CD38-CD45RA−CD90+CD49f+ cells were isolated by FACS after 10 days in co-culture with MPCs, SFV and VPA. These isolated cells were then cultured in MethoCult™ H4435 Enriched (Stem cell Technologies), which is a complete methylcellulose-based medium containing IL-3, IL-6, G-CSF, GM-CSF, SCF and EPO and useful for growth and enumeration of hematopoietic progenitor cells in colony-forming unit (CFU) assays). Colonies were scored on day 14 of culture and tested for colony forming efficiency. As shown in FIG. 11, the isolated CD34+CD38-CD45RA−CD90+CD49f+ cells contained clonogenic hematopoietic progenitors which gave rise to erythroid progenitor cells (BFU-E), granulocyte-macrophage progenitor cells (CFU-GM, CFU-G and CFU-M), and multipotential granulocyte, erythroid, macrophage and megakaryocyte progenitor cells (CFU-Mix). Overall colony forming efficiency was 0.42%.

Example 3: Expansion of CD34+ Cells from Peripheral or Cord Blood

About 25 million MPCs are culture expanded in animal component free media for about 5 days to obtain a cell population comprising about 400-500 million MPCs. The MPCs are then washed and placed into co-culture with about 50 million CD34+ cells obtained from the peripheral blood of a subject in need of an HSC transplant, or from cord blood. At this stage there would be approximately 2.5 million primitive HSCs of the phenotype CD34+CD45RA−CD90+CD49f+ within the total CD34+ population. The cells are then co-cultured in serum-free media in the presence of an HDAC inhibitor for a period of about 10 days, after which the HSCs of the phenotype CD34+CD45RA−CD90+ CD49f+ have been expanded to about 100,000,000 cells.

At this stage, the total cell population can be used for administration to the subject in need of an HSC transplant.

Alternatively, the CD34+CD45RA−CD90+CD49f+ cells can be isolated by immunoselection, for example using an antibody which binds to the CD49f antigen, to provide a purified population of these cells which are particularly suitable for long-term renewal and engraftment. The remaining cell population, from which the CD34+CD45RA−CD90+CD49f+ cells have been depleted, is enriched for CD34+ CD49− cells which are particularly useful for early phase neutrophil/platelet recovery.

The immunoselected CD34+CD45RA−CD90+CD49f+ cells can be subjected to genetic modification by, for example, transduction with a viral vector containing a gene sequence encoding a therapeutic protein, or by use of the CRISPR system or the like.

REFERENCES

Ausubel, F. M. (Ed.). (1987 including all updates until present). *Current Protocols in Molecular Biology*. New York: John Wiley & Sons.

Brown, T. A. (Ed.). (1991). *Essential Molecular Biology: A Practical Approach* (Vol. 1 and 2). Oxford: IRL Press at Oxford University Press.

Coligan, J. E., Kruisbeek, A. M., Margulies, D. H., Shevach, E. M., & Strober, W. (Eds.). (1991 including all updates until present). *Current Protocols in Immunology*. New York: John Wiley & Sons.

Glover, M., & Hames, B. D. (Eds.). (1995 and 1996). *DNA Cloning: A Practical Approach* (Vols. 1-4).

Gronthos (2003). *Journal of Cell Science,* 116(Pt 9), 1827-1835.

Gronthos & Simmons (1995). *Blood,* 85(4), 929-940.

Harlow, E., & Lane, D. (1988). *Antibodies: A Laboratory Manual*. New York: Cold Spring Harbor Laboratory Press.

Perbal, B. V. (1984). *A Practical Guide to Molecular Cloning*. New York: Wiley.

Sambrook, J., & Green, M. R. (2012). *Molecular Cloning: A Laboratory Manual* (*Fourth Edition*). New York: Cold Spring Harbour Laboratory Press.

Zannettino et al., (1998). *Blood,* 92(8), 2613-2628.

The invention claimed is:

1. A method of expanding hematopoietic stem cells, comprising culturing a population of hematopoietic cells in the presence of mesenchymal lineage precursor or stem cells (MLPSCs) which express TNAP or undifferentiated progeny thereof and at least one histone deacetylase inhibitor (HDACi) such that hematopoietic stem cells having the phenotype CD34+ are expanded when compared to the population of hematopoietic cells prior to culturing in the presence of mesenchymal lineage precursor or stem cells (MLPSCs) and at least one histone deacetylase inhibitor (HDACi).

2. The method of claim 1, wherein hematopoietic stem having the phenotype CD34+, CD90+ are expanded at least 5-fold.

3. The method of claim 1, wherein the HDACi is selected from the group consisting of valproic acid (VPA), trichostatin (TSA), DLS3, MS275, Suberoylanilide Hydroxamic Acid (SAHA), and HDAC6 inhibitorl61.

4. The method of claim 1, wherein the hematopoietic cells are also cultured in the presence of one or more growth factors selected from the group consisting of stem cell factor (SCF), flt3 ligand (FL), thrombopoietin (TPO), IL3 and IL6.

5. The method of claim 1, wherein the hematopoietic cells are also cultured in the presence of one or more stem cell renewal agents selected from the group consisting of StemRegenin (SR1) and UM171.

6. The method of claim 1, wherein the MLPSCs are isolated by immunoselection and culture expanded.

7. The method of claim 1 which further comprises isolating cells having the phenotype CD34+, CD90+ following culture expansion to provide an enriched population of cells having the phenotype CD34+, CD90+.

8. The method of claim 7 which further comprises removing cells having the phenotype CD34+, CD45RA−, CD90+, CD49f+ following culture expansion to provide an enriched population of cells having the phenotype CD34+, CD49f−.

9. The method of claim 7 which further comprises introducing a heterologous nucleic acid into enriched cells having the phenotype CD34+, CD90+.

10. The method of claim 8 which further comprises introducing a heterologous nucleic acid into enriched cells having the phenotype CD34+, CD49f−.

11. The method according to claim 1 wherein the MLPSCs comprise a heterologous nucleic acid molecule which is transferred to the hematopoietic stem cells having the phenotype CD34+, CD45RA−, CD90+, CD49f+ during culture expansion.

12. The method of claim 2, wherein hematopoietic stem cells having the phenotype CD34+, CD90+ are expanded at least 10-fold.

13. The method of claim 12, wherein hematopoietic stem cells having the phenotype CD34+, CD90+ are expanded at least 20-fold.

14. The method of claim 13, wherein hematopoietic stem cells having the phenotype CD34+, CD90+ are expanded at least 40-fold.

15. The method of claim 2, wherein hematopoietic stem cells having the phenotype CD34+, CD45RA−, CD90+, CD49f+ are expanded at least 5-fold.

16. The method of claim 15, wherein hematopoietic stem cells having the phenotype CD34+, CD45RA−, CD90+, CD49f+ are expanded at least 10-fold.

17. The method of claim 16, wherein hematopoietic stem cells having the phenotype CD34+, CD45RA−, CD90+, CD49f+ are expanded at least 20-fold.

18. The method of claim 17, wherein hematopoietic stem cells having the phenotype CD34+, CD45RA−, CD90+, CD49f+ are expanded at least 40-fold.

19. The method of claim 7, wherein isolated cells and the enriched population of cells have the phenotype CD34+, CD45RA−, CD90+, CD49f+.

20. The method of claim 19, which further comprises removing cells having the phenotype CD34+, CD45RA−, CD90+, CD49f+ following culture expansion to provide an enriched population of cells having the phenotype CD34+, CD49f−.

* * * * *